US008639524B2

(12) United States Patent
Solomon

(10) Patent No.: US 8,639,524 B2
(45) Date of Patent: Jan. 28, 2014

(54) SYSTEM FOR INTELLIGENT MEDICAL DEVICE NETWORK

(76) Inventor: Neal Solomon, Oakland, CA (US)

( * ) Notice: Subject to any disclaimer, the term of this patent is extended or adjusted under 35 U.S.C. 154(b) by 1206 days.

(21) Appl. No.: 12/462,793

(22) Filed: Aug. 7, 2009

(65) Prior Publication Data

US 2010/0070054 A1     Mar. 18, 2010

Related U.S. Application Data

(60) Provisional application No. 61/188,379, filed on Aug. 8, 2008.

(51) Int. Cl.
G06Q 10/00     (2012.01)
G06Q 50/00     (2012.01)
A61B 5/00      (2006.01)

(52) U.S. Cl.
USPC .................................... 705/2; 705/3; 600/300

(58) Field of Classification Search
USPC .......................................... 705/2, 3; 600/300
See application file for complete search history.

(56) References Cited

U.S. PATENT DOCUMENTS

| | | | | |
|---|---|---|---|---|
| 5,569,186 A | * | 10/1996 | Lord et al. | 604/67 |
| 6,669,631 B2 | * | 12/2003 | Norris et al. | 600/300 |
| 7,127,299 B2 | * | 10/2006 | Nelson et al. | 607/60 |
| 2007/0122824 A1 | * | 5/2007 | Tucker et al. | 435/6 |

OTHER PUBLICATIONS

Pickup, John, "Continuous Subcutaneous Insulin Infusion at 25 Years," Mar. 2002, Diabetes Care, vol. 25, No. 3, p. 593-598.*

* cited by examiner

*Primary Examiner* — Sind Phongsvirajati
*Assistant Examiner* — John Go

(57) ABSTRACT

The system organizes a network of intelligent medical devices (iMDs) for diagnostic and therapeutic functions. The iMD network uses distributed computing functionality to share logic and memory operations. The system uses wires and tubes to connect (a) iMDs between each other, (b) iMDs and sensor probes and (c) internal iMDs and external devices, including computers. The ability to network the iMDs expands the functionality between the iMDs. The iMDs share specialized functions, and multitask, to solve complex medical problems.

19 Claims, 25 Drawing Sheets

SYSTEM FOR INTELLIGENT MEDICAL DEVICE NETWORK

CROSS-REFERENCES TO RELATED APPLICATIONS

The present application claims the benefit of priority under 35 U.S.C. §119 from U.S. Provisional Patent Application Ser. No. 61/188,379, filed on Aug. 8, 2008, the disclosure of which is hereby incorporated by reference in their entirety for all purposes.

FIELD OF THE INVENTION

The invention involves micro electro mechanical systems (MEMS) applied to medical devices and components. The system involves the networking of multiple medical devices. The invention applies to diagnostic and therapeutic aspects of medical intervention.

BACKGROUND

As scientists discover the mechanics of genetic processes, our understanding of the sources of diseases increases. The benefits of understanding genetic dynamics and proteomics regulatory processes assists in development of a new generation of medical devices able to diagnose, regulate, manage and cure complex diseases. The potential exists to develop personalized drug therapies to target specific genetic pathologies.

Regarding diagnostic systems, MEMS is an umbrella for a class of new medical devices able to identify genetic mutations and proteomic dysfunctions. While largely external in vitro devices, DNA microarrays, RNA microarrays and protein microarrays provide feedback to identify an individual's genetic information. Protein microarrays use antibodies to assess protein functional responses. In addition, whole cell assays test cells with analytes to assess specific responses to chemical inputs. Multi-phenotype cellular arrays are used for bio-sensing of specific inputs in order to study cell functions.

Though DNA, RNA, protein and whole cell arrays have developed separately, a new generation of lab on chip (LOC) and micro-total analysis systems (µTAS) technologies have emerged as well that integrate several functions in a single device. These multi-purpose arrays provide clinical diagnostic data to practitioners.

In addition to these external devices, the evolution of radiological diagnostic tools has provided a revolution to analytical practitioners. In particular, the use of CT, PET and MRI technologies provides detailed data on specific disease progression. In addition to these external radiological diagnostic technologies, the internal sensing "pill" camera records and transmits digital images to substitute for the surgical intervention of exploratory surgery. Finally, the use of implanted sensors assists in the regulation of simple deterministic expert systems.

The convergence of nanotechnology with biology has produced "bionano" devices. In the main, the use of nanotechnology is limited to particles that are targeted to specific tissue in order to identify pathology and, when combined with directed radiation, provide a therapeutic alternative. The advent of self-assembled peptide nano-biomaterials provides interesting opportunities for diagnostics and therapeutics. The use of nano-scale devices, in which collective behaviors are controlled for therapeutic as well as diagnostic modes, provides an advancement of the bionano field.

Regarding therapeutic medical devices and systems, the field has evolved from the development of the hearing aid and the cardiac pace maker. For instance, the implantable brain pacemaker has been developed to regulate epileptic energy pulses and blood glucose monitoring is regulated with an insulin pump. Moreover, implantable pain management devices are used to control chronic pain. Microfluidic devices to target drug delivery, primarily using a deterministic expert system control model, have also been developed. All of these devices are simple single-function mechanisms targeted to a specific disease or disorder.

An emerging scientific field is providing a new set of technologies from bio-inspired computing. Complexity science deals with self-organizing systems that learn in indeterministic environments. The inspiration from the autonomic nervous system and the human immune system provide computing systems that emulate these complex biological processes. Autonomic computing self-diagnoses, self-heals and self-regulates distributed networks. The human immune system provides inspiration for immunocomputing models that emulate protein regulatory network behaviors in order to solve complex optimization problems. Swarm intelligence metaheuristics provides solutions to optimization problems as well. For instance, the ant colony optimization (ACO) metaheuristic provides a model to solve network computing problems. These models share the ability to develop solutions to problems in self-organizing systems, including plasticity behaviors, in indeterministic environments. In effect, these complex computing and control systems learn. So far, these complex computing models have not been applied to medical devices.

The ability to use genetic and proteomic information to solve complex pathologies provides a new generation of opportunities to build medical devices that are customized to each individual's specific disease(s). Our understanding of cancer, for instance, as the combination of multiple genetic mutations, suggests that each disease type is classed into a typology that can be solved with specific targeted therapies. Given this new knowledge, it is logical to build medical devices that are personalized to specific diseases of each individual. In particular, the use of medical devices focused on solving problems involving pathologies associated with cardiovascular, neurological, immunological and endocrinological systems, and with cancer, is a next step.

Each of the prior medical devices has limitations. For the most part, none of the implantable medical devices are "intelligent". Rather, they are simple deterministic systems. They are also single function devices focused on a specific narrow medical problem. Because they are merely deterministic expert systems, they do not combine diagnostic and therapeutic functionality. In the diagnostic mode, they do not provide sophisticated modeling functions. Further, prior MDs are not networked since they typically involve a single device performing a single function. Finally, these devices are not useful in personalized medicine, which require complex analysis and targeting of individual therapies to unique problem sets.

What is needed? We need active intelligent medical devices that are able to work with other medical devices to solve multiple medical problems. We need complex medical devices that are capable of integrating diagnostics and therapeutics in order to maximize efficiency, to promote early detection and treatment and to modify functionality with feedback mechanisms to solve complex biological optimization problems in biological regulatory networks. The present system develops an intelligent multifunctional medical device system.

PROBLEMS THAT THE SYSTEM SOLVES

The present system solves a range of problems. How can we develop an intelligent medical device (iMD) that coordinates diagnosis and therapy? How can the iMD coordinate sensors and integrated circuits? How is the processing of chemical and biological fluids administered by using the iMD? How is the implantable iMD coordinated with external computation and modeling? How does the device collect samples and data in real time? How does one integrate multi-functionality into an efficient iMD design? How is the implantable device installed with minimal invasiveness? How are nano-components integrated into the iMD? How does the iMD use sensors and probes for maximum effect? How does the iMD efficiently analyze biological data? How are solutions to complex problems developed and refined in the iMD? How is drug delivery optimized in the iMD? How can we construct customized drugs for therapies to individual patient pathologies? How can an iMD self-organize and adapt to indeterministic environmental conditions? How can multiple iMDs be coordinated, particularly for multiple applications? Solving these problems presents opportunities to develop a new generation of highly effective medical devices.

SUMMARY OF THE INVENTION

The present system organizes a network of iMDs. The network links multiple iMDs for specific diagnostic and therapeutic functionality. The system uses distributed computing mechanisms to share logic and memory operations among the internal iMD network, including database storage capabilities, between the devices.

The iMD network connects iMDs and sensor probes used for data collection. The system is also connected to external devices, such as substantial computation resources, in order to supplement the limited internal computers.

The iMDs are connected to each other by a network of wires and tubes. The wires maintain interaction between the iMDs and internal devices, while the tubes have access to devices for fluidic delivery and evacuation. This function enables diagnostic and therapeutic operability.

The iMD network continuously rebalances the computation, diagnostic and therapeutic functions of the overall system by sharing specialized resources of each node. When one iMD requires more resources to solve a problem, it requests the supplemental resources from other iMDs and from external suppliers. The networking capabilities enhance multi-functionality in the iMD system. Taken together, the network dynamics of the iMD system present self-organizing processes.

Novelties

The present invention applies network computing architecture to the iMD system operation. Network computing technologies provide the inspiration for the organization, and reorganization, of multiple iMDs and components. By coordinating multiple iMDs, the functionality of the devices are maximized. In this way, multiple biomedical problems are solved simultaneously.

Organized in networks, iMDs are smart adaptive systems that are modular, flexible, integrated and customized.

ADVANTAGES OF THE INVENTION

There are a number of advantages of the present invention. The combination of multiple iMDs provides a sophisticated network of devices to solve complex biomedical problems. Because they are combined in networks, the system presents critical redundancies that provide a failsafe against malfunction. Multiple iMDs in networks also provide more computation resources to more rapidly diagnose and solve complex problems.

While they use multiple devices and elements, the network also minimizes lags in responding to a problem. Since iMDs are positioned in multiple physiological spaces, access to multiple tissues is provided, which enables management of complex biological systems. Because of these networking features, the system is able to solve multiple problems simultaneously.

DESCRIPTION OF THE INVENTION

(I) Network iMD System Models

There are several main models for the organization of multiple iMDs into a network. First, a single central device is dominant and controls primarily specialized devices. Second, multiple iMDs are distributed in a node-to-node system. Third, a network is organized in which the dominant node shifts periodically. Fourth, the internal iMD network is integrated with an external system, which behaves as the dominant control center.

(1) System for Network of Specialized Single Function iMDs

In a network of iMDs, specific single function devices interoperate. In this model, the specialized single function iMDs perform diagnostic or therapeutic functions. When they operate in concert, the multiple single function iMDs work together in a division of labor, sharing functionality as a single multifunctional iMD.

An example of this model specifies several different types of diagnostic iMDs, each with a different type of microarray for testing different media. Each iMD collects and tests different types of biological samples. Further, the system in this example uses different specialized therapeutic iMDs that target specific tissues. The various specialized diagnostic iMDs work in conjunction with the multiple specialized therapeutic iMDs to perform different tasks. One advantage of this approach is the ability to precisely target a specific disease or tissue. The ability to program multiple single function devices with similar tasks also produces system redundancies that resist failure of any one part.

Another advantage of this approach is that the iMDs may be very small and efficient. The networking of a number of these iMD nodes produces a self-organizing system that shares data and active functionality. This model emulates bio-inspired approaches of ants and bees, which divide out simple functions among specialists that work together to accomplish a task.

A sensor network is organized by the specialized iMDs to transfer active functionality to the best device that is able to complete a mission at any specific time.

The organization of the overall network of iMDs produces a system that is more successful at solving problems than a single iMD in most cases.

In another embodiment of this approach of using specialized nodes, the system includes a single central multi-functional iMD to control the organization and reorganization of the network.

(2) System for Network of Multi-Functional iMDs for Synchronized Evolvable Hardware Networking several multi-functional iMDs provides substantial flexibility to simultaneously solve multiple diagnostic and therapeutic problems. In this approach, the multi-functional devices are organized to operate independently. However, since the multi-functional iMDs consist of multiple integrated and synchronized modules, the reorganization of the network of devices continuously solves optimization problems that employ numerous components. As the demands of the environment change, the combinatorial options of the shifting configurations of the network over time are efficiently organized. This model maximizes the self-organizational capacities of the iMD network for aggregation and reaggregation processes based on function and demand.

The network of multi-functional iMDs may be structured with multiple interoperating independent nodes or with a central iMD to control the overall system. In this model, each specific iMD may maintain satellite components for which it preserves control even as the whole system constantly restructures its priorities. One advantage of this model is the ability to have different iMDs provide overflow diagnostic, modeling and therapeutic functionality, particularly useful in time-sensitive situations. In this sense, multiple components within iMDs, such as diagnostic or computational modules, are interchangeable, thereby proving essential failsafe processes.

Since the multi-functional iMDs integrate several functional modules, they share functionality by combining complex processes in the network. Multiple therapeutic modules, for example, combine to perform specific operations, such as to provide sustained drug delivery that may be beyond the capacity of a single iMD alone.

Further, multiple multi-functional iMDs are combined for multiple purposes to simultaneously solve multiple problems simultaneously. When configured with multiple multi-purpose iMDs, the network is able to simultaneously diagnose multiple problems while at the same time providing different drug combinations to multiple pathologies. This configuration mode provides powerful set of tools to practitioners as they seek to solve and manage complex pathologies.

(II) Distributed Computing in iMD Network (3) Method for Sharing Computation Between iMDs Regardless of the network configuration of the iMDs, the system shares computation resources. The network computing aspect of the iMD system provides multiple operational advantages. The most notable advantage of network computing in a system of iMDs is the ability to share computation resources between devices in order to maximize computability. While each device maintains the efficiency use of its semiconductors in order to preserve power, the ability to share computing resources substantially benefits the overall system.

By sharing computation, the system is able to perform multiple functions simultaneously. The system collects data at one location, diagnoses the data at another location, develops complex models by splitting the modeling function between multiple devices, and then delivers drugs to multiple locations simultaneously to solve a complex problem.

Though the network computing function of the iMD system maximizes efficiencies, the internal system also interacts with external computing resources. The system receives periodic software updates, for example. The system also backs up its memory by using off site computer memory. In addition, the system uses external computing resources for extensive modeling functions.

The coordination of the internal iMD computing network with the external computing system allows the iMD system to solve immediate optimization problems while behaving in real time to treat pathologies and also simultaneously modeling problems to seek solutions by using substantial external computing.

The application of a network computing model to the iMD system allows the distributed system to extend functionality beyond a single device. The distributed computing approach allows the overall system to coordinate the functions of specific computing devices and components in each iMD so as to maximize system performance. For instance, when several iMD computing devices are operating at maximum capacity to solve different problems, the computing devices of other iMDs are accessed in order to provide analytical resources. In one example of this approach, the shared computing functionality of multiple iMDs perform modeling of multiple problems simultaneously. This model is also similar to the use of multi-core computing devices, but in the present example the integrated circuits are in multiple distributed devices.

This approach shifts the load to the simplest device capable of solving the problem. For instance, if a set of FPGAs can solve a problem, then this is preferred to using one or more SoCs to solve the problem, thereby preserving computing capacities.

(4) Method for Coordination of Distributed Computing in iMD System Scheduling Algorithms The iMD network shares both computer logic capacity and computer memory capacity among iMD nodes. In sharing logic functionality, the system networks the SoC's in each iMD to balance the computing load overall. The system uses scheduling algorithms to shift computing from iMDs that have maximum loads at a specific time to those that have excess capacity, for instance, if they are not performing multiple simultaneous tasks.

In sharing memory functionality, the system stores and accesses data in multiple devices in the network in order to maximize the memory system overall as well as to build in redundancies; if a node is disabled, the memory is preserved. While this approach is redundant, it provides an important failsafe.

In order to maximize the use of logic and memory computing functions, the system uses a queuing approach in a distributed computing network. While this approach begins with a first in first out (FIFO) model, more important priorities are continuously put at the front of the line. This model balances the traditional computing operations with the mission critical functional components.

The use of scheduling algorithms is also applied to sensor networks, which are coordinated by the computing system in order to organize and optimize diagnostic functions.

By using scheduling algorithms to prioritize and reprioritize the logic and memory computing functions as well as the diagnostic and therapeutic functions of the iMD network, the overall system is continuously optimized and reorganized for maximum effect.

(5) System for Distributed Databases in iMD Network

Each iMD maintains a database in order to store and access data sets. The database is a central computing component used in the analytical processes of solving biomedical problems. The present invention uses a distributed database model within the iMD network to maximize functionality across the system. While data is stored and accessed within each iMD database to control the functions of each iMD, each device is also able to access the databases of other iMDs. This distributed network accessibility allows the system to extend the range of logical analysis beyond a single iMD and thereby substantially increases functionality of the overall system.

In addition to using databases within the internal iMD network, the system also uses databases in external computing systems. This approach preserves the computing resource constraints of the internal system while maximizing the external computation.

(6) System for Wireless iMD Networks

In order to share computation resources in the internal iMD network, the system uses wireless communications functionality. Each iMD uses an antennae to send and receive signals to other iMDs and to external communications devices. In order to minimize power usage, the system uses the wireless function sparingly, sending efficient signals to other internal iMDs on demand and sending signals to external communications devices at regular intervals. Similarly, the system receives regular communications at specific times from external sources, particularly with updated program code.

In addition to providing wireless communications between iMDs, the system also provides wireless communications between sensors and iMDs. Sensor networks communicate with wireless functionality as they are activated. Once activated by a trigger event, the sensors provide data to iMDs.

In an alternative embodiment, the system uses radioisotope fueled cells which use radioactive electron emitting isotopes that continuously recharge batteries, thereby allowing the batteries to maintain power for decades. This application is useful for implantable iMDs.

(III) Interconnects Between iMDs

While wireless communications between iMDs is possible, it is generally problematic in implantable devices without extremely long battery capacity. The alternative mechanism for communication is therefore to use hard wired interconnects between iMDs.

The present invention uses micro scale "tubes" to enclose wires, fiber optic cables and smaller tubes. The system then connects wires between the multiple devices in the network for communications.

(7) System and Apparatus for Micro-Scale Wires Between iMDs

The system uses micro-scale wires to communicate between iMDs, between iMDs and ancillary devices like probes and drug cargo delivery vehicles and between iMDs and external computer resources. The micro-scale wires connect to the computing modules of iMDs for rapid communication and analysis.

In the diagnostic mode, probes gather external biological data and send the data to iMDs for analysis via wires or fiber optic cables.

Access to external computer resources by using the network of wires allows the iMD system to have substantial computability for analyses and modeling to solve complex optimization problems while the iMD network is processing other therapeutic functions.

(8) Inter-iMD Network of Tubes

Though the micro-scale wires are used directly between devices, they are integrated into the micro scale tubes that enclose the wires. These tubes are expandable and flexible in order to accommodate pressure in their environment.

The micro scale tubes have smaller integrated tubes inside for different functions. For instance, in the therapeutic mode, the smaller tubes are used to deliver drugs to a specific site, while parallel tubes extract chemicals from tissues. The smaller tubes are used to send probes to, and extract probes from, specific targeted locations as well. The micro-scale wires in the tubes are used for communication between iMDs and between iMDs and probes.

The tubes connect between internal iMDs and external iMDs, reservoirs and satellites. These tubes are critical for refilling drugs, chemicals, agents and biologicals. They are also used to evacuate fluids and cells from the iMD after performing a function.

The combination of internal iMD network with the external iMDs provides a complex self-organizing system.

(9) Multifunctional Parallel Network of iMD Tubes

Because they are multifunctional, the multiple tubes are useful for diagnostic, therapeutic and communications functions. The smaller tubes that are focused on each of these functions are connected to different modules in the iMD. For example, the smaller tube that is used to send and retrieve probes is attached to the diagnostic module. Further, the smaller tube used to send drugs and extract chemicals are attached to the therapeutic module. In addition, tubes are attached from the extraction site of tissue directly to a separate reservoir, thereby bypassing the iMD. Local area probes are connected at nearby tissue.

(10) Functional Modularity in Networks for Reaggregation of iMD System

Since it consists of a network of multifunctional iMDs, the system modulates its functions across the multiple devices in the network. The analogy of this operational functionality is to cloud computing in a distributed network. When one iMD is dysfunctional, the system re-routes around the device and balances the load using optimization algorithms.

As demands are put on the system by analytical, diagnostic and therapeutic functions, the system constantly restructures its priorities. This process of continuous restructuring of functions to multiple multifunctional devices based on changing priorities forms a reaggregation model. The system is constantly reorganizing its overall functionality to seek equilibrium. Ultimately, once the devices succeed in eliminating the patient's pathologies, the devices have accomplished their tasks and return to a stable equilibrium.

(11) Multitasking of Multiple iMDs

The iMD network is useful in coordinating the interaction of multiple components to simultaneously address parallel pathologies. The distributed iMD network is organized to solve multiple optimization problems at the same time by concurrently employing the operations of the computational components, diagnostic components, and therapeutic components. As feedback from multiple processes is received from the external environment, the system learns and restructures to maximize overall network functionality. Given the present network model, the iMD system is ideal for fighting two or more pathologies at the same time by sharing resources.

(12) Main iMD System Configurations

The iMD system is modular. Consequently, the system is commercially produced in several classes of configuration. In the first configuration, the system consists of a single iMD. It is mass produced, non-reconfigurable and simply dispenses drugs in a feedback system with deterministic functionality. This initial level of the commercial iMD has limited diagnostics and therapeutic functionality and is restricted to connections with wired probes through connected tubes. This device also has relatively restricted computation capabilities. The main application of this device is for a single pathology, though each device is configured specifically for a patient's unique condition. Because of its limited functionality, it is reasonably priced. This device is intended for mass appeal.

In the second configuration, the system consists of multiple iMDs. The iMD network has multiple functionalities to interact with multiple pathologies. This integrated system has advanced computation for on-board analytical functionality in indeterministic environments and is connected to external devices as well. The system uses a network of tubes to connect the iMDs and also uses wired probes for data collection. The system requires surgical (endoscopic) implantation and periodic physician servicing. This initial network configuration has significant functionality and is moderately priced.

In the upgraded configuration, the system consists of multiple iMDs in its most robust configuration. This iMD network has maximum functionality to solve a host of diseases simultaneously. The system has highly advanced computation for analysis and modeling of diagnostic functions, including anticipation of disease progression. The iMD system is fully integrated with external reservoirs, satellites and computation for evacuation, refilling and parallel computer modeling. This advanced system uses multiple nano- and micro-robotics elements for advanced diagnostic and therapeutic functionality and requires periodic surgical intervention. It is used in the most difficult cases for critical care and for solving the most complex multivariate medical problems. This expanded version of the iMD system is not price sensitive.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

DETAILED DESCRIPTION OF THE DRAWINGS

A single intelligent medical device (iMD) has multifunctional capacities to perform analytical, diagnostic and therapeutic functions by combining multiple functional modules in a single device that interacts with, and provides therapeutic utility for solving, medical pathologies. Multiple iMDs in combination, however, extends the analytical, diagnostic and therapeutic functionality appreciably. Since the iMDs combine several modules in a single device, the combination of iMDs and satellite medical devices into a network provides a complex system of medical devices that are able to simultaneously solve multiple medical pathologies efficiently. Like a computer network, a system of interacting iMDs and satellite medical devices and components efficiently solve complex and adaptive problems.

Figure 1:
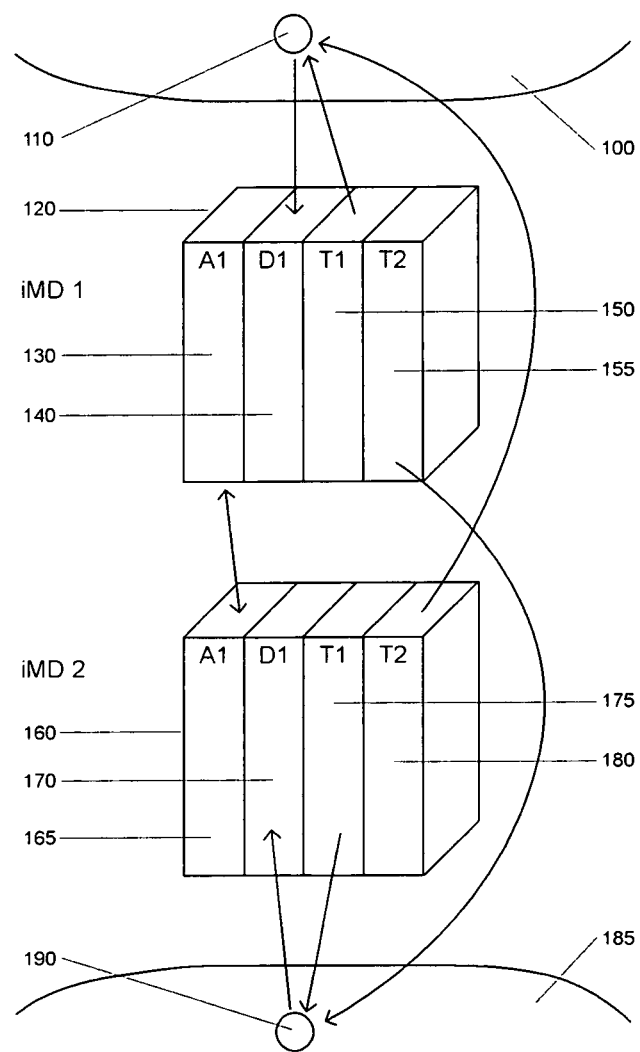
FIG. 1 is a schematic diagram showing interaction of multiple components of two iMDs solving two problems simultaneously.

FIG. 1 shows two modular iMDs interacting with two separate pathologies. IMD 1 (120) and iMD 2 (160) share analytical data between 130 and 165. The diagnostic module (140) of iMD 1 interacts with the pathology (110) in a tissue (100) site while the diagnostic module (170) of iMD 2 interacts with the pathology (190) in another tissue (185) site. The therapeutic module 1 (150) of iMD 1 addresses the pathology at the first cell site (110) while the therapeutic module 1 (175) of iMD 2 addresses the pathology at the second cell site (190).

Since the iMDs share data, they are also able to share the therapies. Therapeutic module 2 (155) of iMD 1 applies a therapy to the second cell site (190) while the therapeutic module 2 (180) of iMD 2 applies a therapy to the first cell site (110). The sharing of information, modeling, diagnostics and therapeutics between iMDs demonstrates that the iMD network works as a system.

Figure 2:
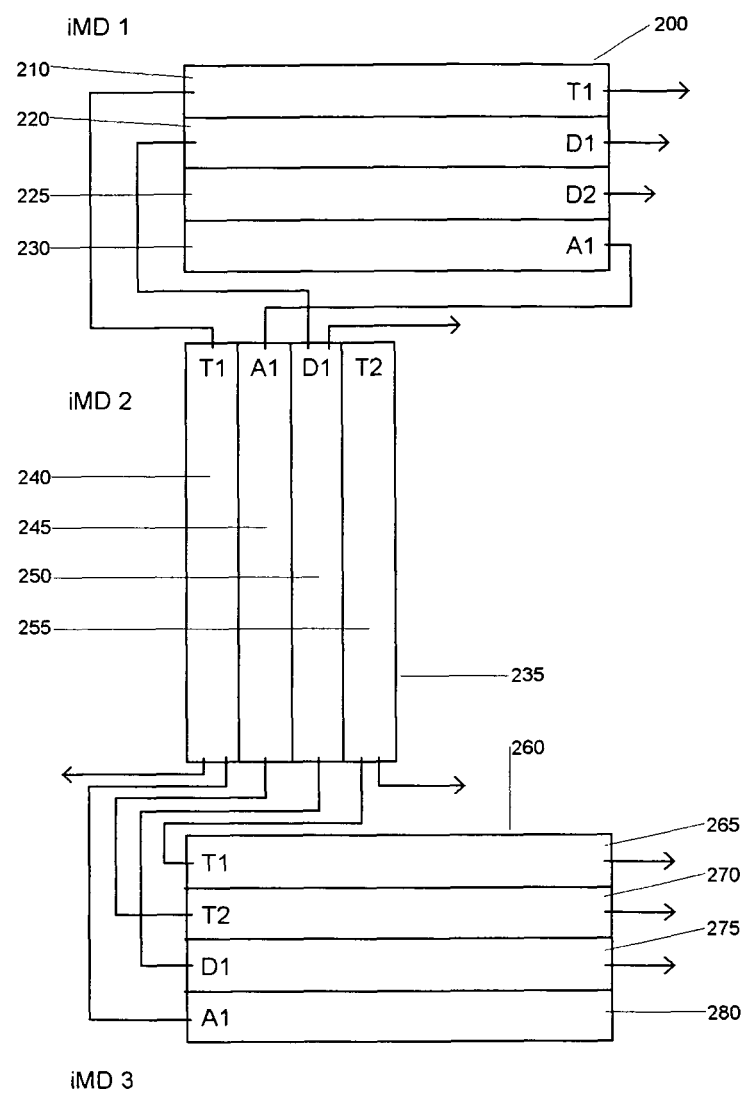
FIG. 2 is a schematic diagram showing the side views of three interconnected iMDs in a multifunctional network.

In FIG. 2 illustrates a view of the interconnections between three iMDs. IMD 2 (235) connects its analytical, diagnostic and therapeutic modules (240-255) to the analytical, diagnostic and therapeutic modules (210, 225 and 230) of iMD 1 (200) and to the analytical, diagnostic and therapeutic modules (265-280) of iMD 3 (260).

Figure 3:
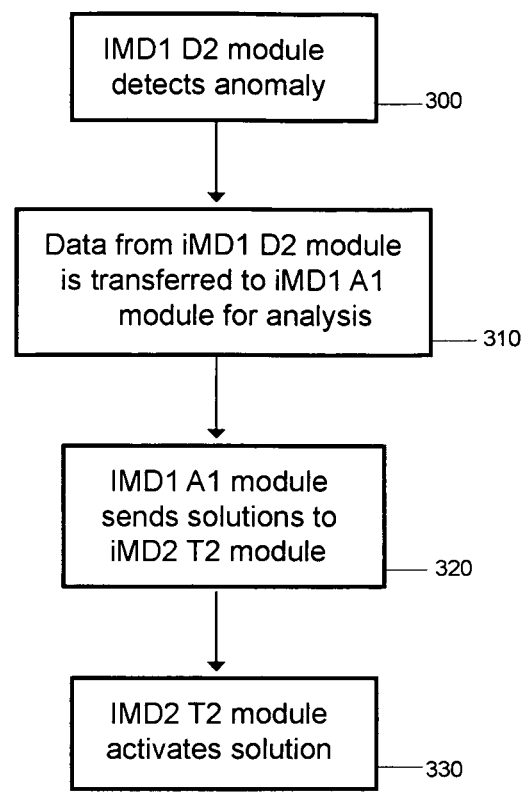
FIG. 3 is a flow chart describing the process of components of two iMDs working together to solve a problem.

FIG. 3 shows the process of components from different iMDs working together to solve a problem. After an anomaly is detected by iMD 1 module D2 (300), data from iMD 1 module D2 is transferred to iMD 1 module A1 for analysis (310). IMD 1 module A1 sends solutions to iMD 2 module T2 (320) and iMD 2 module T2 activates a solution (330).

Figure 4:
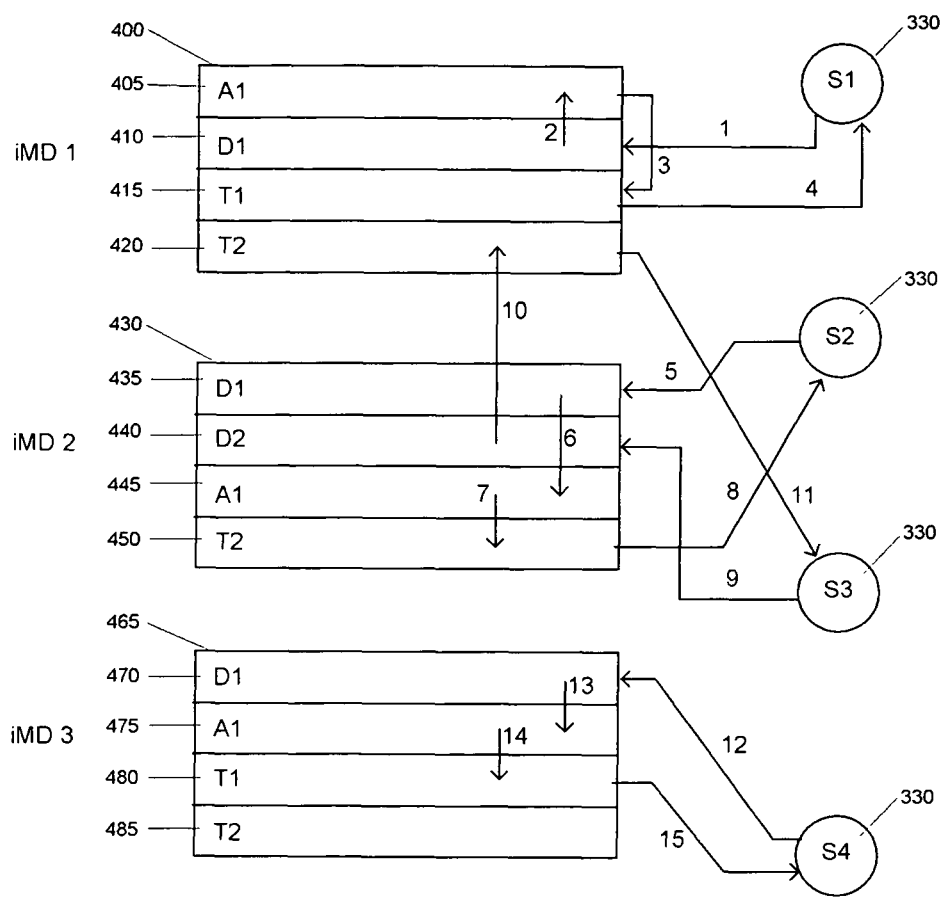
FIG. 4 is a schematic diagram showing the order of operations of three iMDs solving several simultaneous problems.

FIG. 4 shows the order of operations of three iMDs solving several simultaneous problems. IMD 1 (400) obtains data (in the form of a biological sample) from S1 (425) at D1 (410), which analyzes the data and transmits information to A1 (405), which analyzes the data, builds a model and sends the data to module T1 (415). Module T1 of iMD 1 then sends a therapy to S1. A sample is then sent from S2 (455) to iMD 2 (430) module D2, which analyzes the sample and sends data to A1 (445), which analyzes the data, builds a model and sends data to T2 (450), which sends a therapy to S2. At the same time, S3 (460) sends a sample to iMD 2 module D2 (440), which analyzes the sample and sends data to iMD 1 T2 (420), which sends a therapy to S3. Finally, samples are sent from S4 (490) to iMD 3 (465), which analyzes the sample and sends data to iMD 3 module A1 (475), which analyzes the data, develops a model and sends data to T1 (480). T1 then sends a therapy to S4. Note that iMD T2 is held in reserve for surplus operational capacity in this example.

Figure 5:
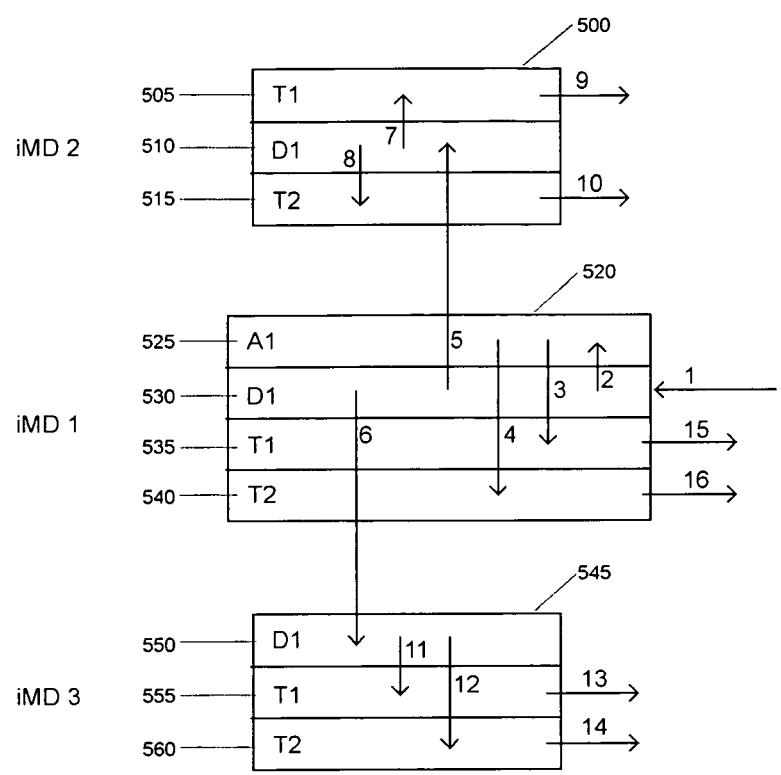
FIG. 5 is a schematic diagram showing the order of operations of a central iMD controlling ancillary iMDs.

In FIG. 5, a central iMD is used to control the interactions between two ancillary iMDs. In this case, iMD 1 (520) receives a sample at D1 (530), analyzes the sample and sends data to A1 (525) for analysis and modeling, which then sends data to T1 (535) and T2 (540). At the same time, iMD 1 D1 (530) sends samples or data to iMD 2 D1 (510) and iMD 3 D1 (550), which conduct analyses of the sample. iMD 2 D1 sends data to T1 (505) and T2 (515), which then provide therapies to pathologies. iMD 3 D1 sends data to T1 (555) and T2 (560), which then supply therapies to pathologies. Finally, iMD 1 T1 and iMD 1 T2 supply therapies to pathologies.

Figure 6:
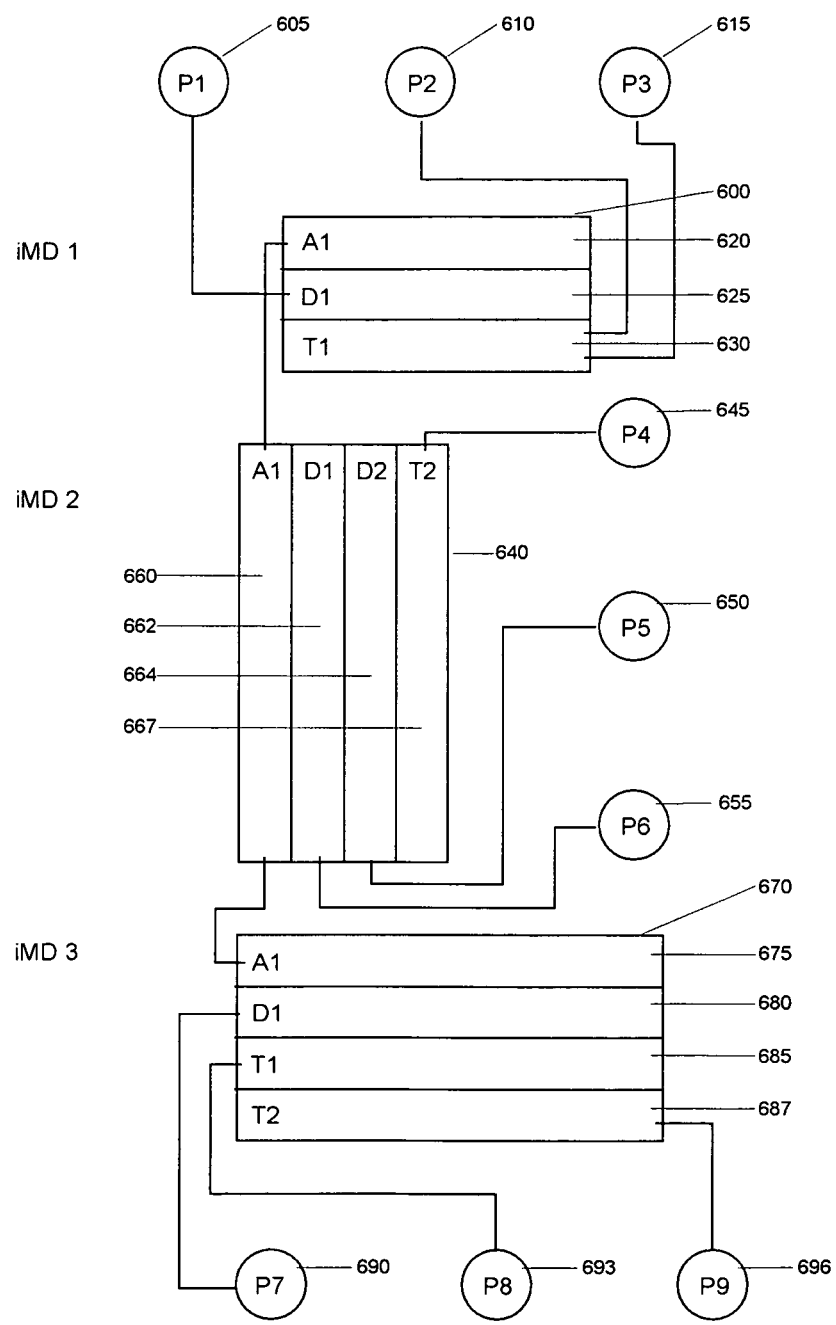
FIG. 6 is a schematic diagram showing the interaction of operations of three iMDs interacting with probes in a network.

FIG. 6 shows the interaction of operations of three iMDs interacting with probes in a network. The analytical modules (620, 660 and 675) of iMD 1 (600), iMD 2 (640) and iMD3 (670) are connected for networking capabilities. P1 (605) provides inputs to the diagnostic module (625) of iMD 1, while the therapeutic module (630) provides outputs to P2 (610) and P3 (615). The diagnostic modules (662 and 664) of iMD 2 obtain inputs from P5 (650) and P6 (655) while the therapeutic module (667) provides outputs to P4 (645). The diagnostic module (680) of iMD 3 provides inputs from P7 (690) while the therapeutic modules (685 and 687) provide outputs to P8 (693) and P9 (696).

Figure 7:
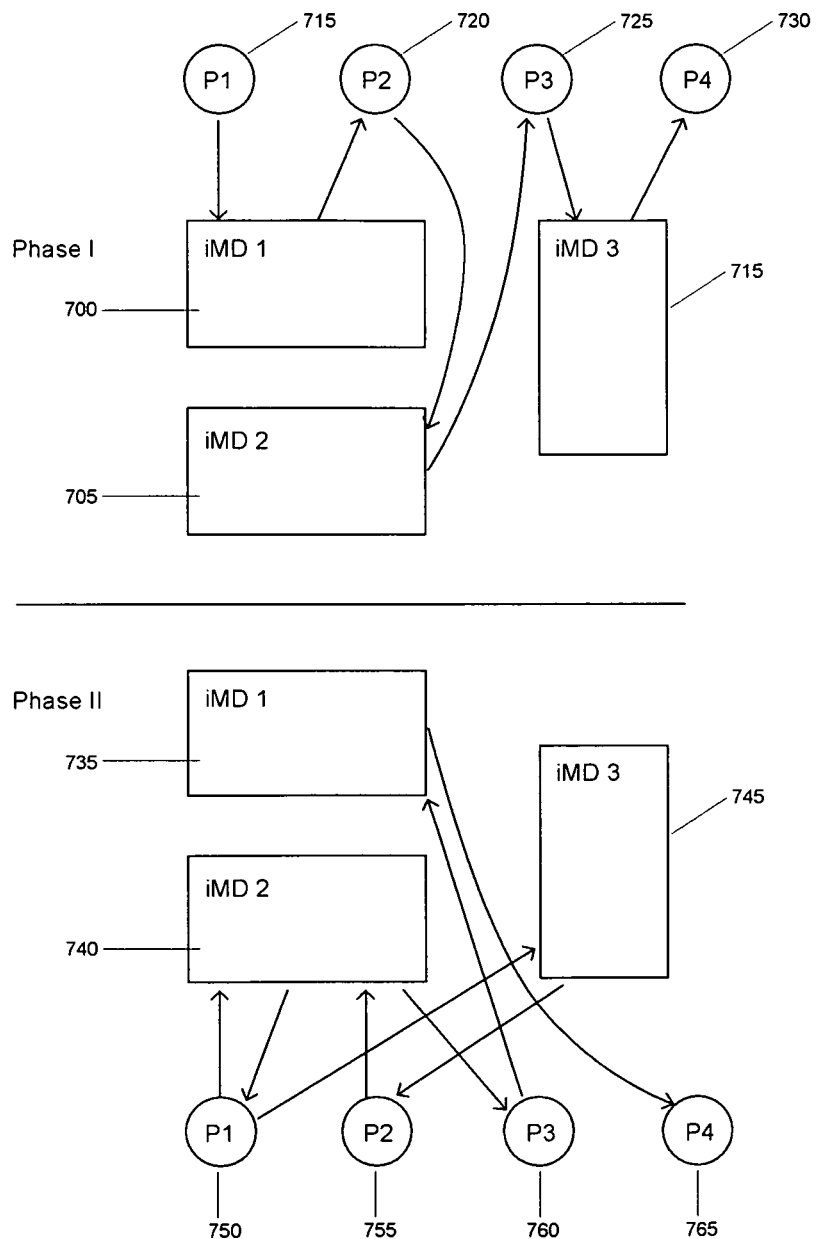
FIG. 7 is a schematic diagram describing the different configuration and order of self-organization of an iMD network.

FIG. 7 shows the different configuration and order of self-organization of an iMD network. In phase I, P1 (715) provides an input to iMD 1 (700), while iMD 1 provides an output to P2 (720) and P2 provides an input to iMD 2 (705). IMD 2 provides an output to P3 (725), which provides an input to iMD 3. IMD 3 (710) provides an output to P4 (730). At phase II, P1 (750) provides an input to iMD 2 (740), which provides an output to P1. P2 (755) provides an input to iMD 2, which provides an output to P3 (760). P3 provides an input to iMD 1 (735), which provides an output to P4 (765). IMD 3 provides an input from P1 and an output to P2. The changing order of treatment of the pathologies with multiple iMDs suggests a multifunctional character of the iMDs to solve different types of transformational problems.

Figure 8:
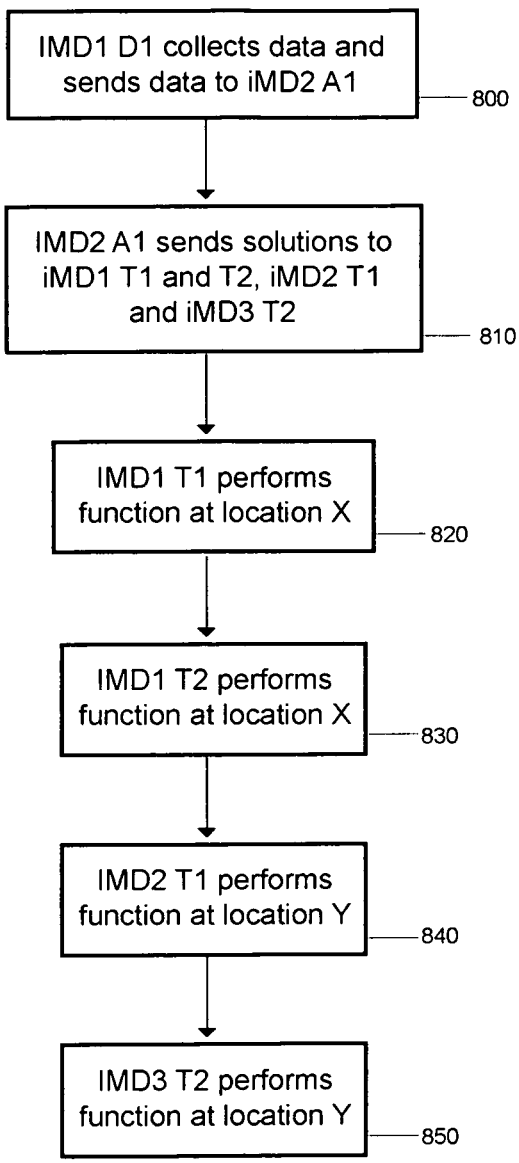
FIG. 8 is a flow chart describing the process of three iMDs performing operations.

FIG. 8 describes the process of three iMDs performing operations. After iMD 1 D1 collects data and sends data to iMD2 A1 (800), iMD 2 A1 sends solutions to iMD 1 T1 and T2, iMD2 T1 and iMD3 T2 (810). IMD 1 T1 performs a function at location X (820) and iMD1 T2 performs a function at location X (830). IMD 2 T1 performs a function at location Y (840) and iMD 3 T2 performs a function at location Y.

Figure 9:
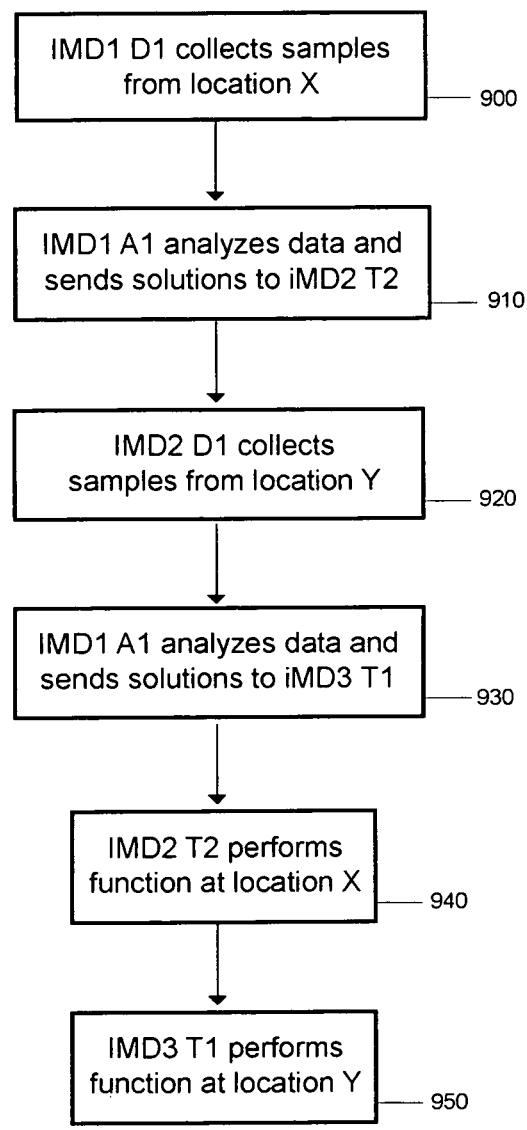
FIG. 9 is a flow chart describing the process of three interacting iMDs to collect, analyze and share sample data.

FIG. 9 describes the process of three interacting iMDs to collect, analyze and share sample data. IMD 1 module D1 collects samples from location X (900) and then iMD 1 A1 analyzes data and sends solutions to iMD 2 T2 (910). IMD 2 D1 collects samples from location Y (920) and sends data to iMD 2 A1 for analysis and sends solutions to iMD3 T1 (930). IMD 2 T2 performs a function at location X (940) and iMD 3 T1 performs a function at location Y (950).

Figure 10:
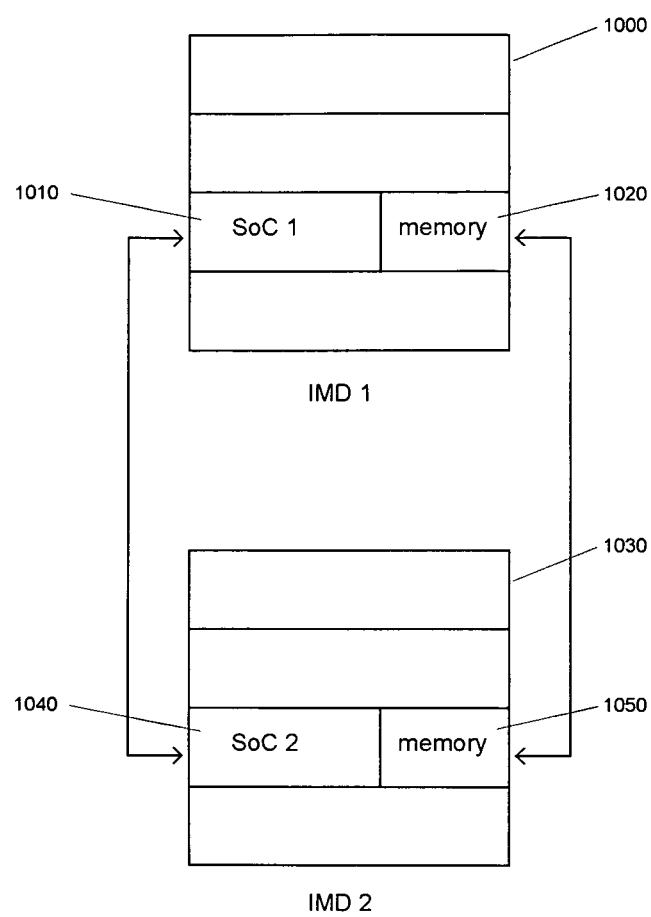
FIG. 10 is a schematic drawing showing the sharing of computation operations between two iMDs.

FIG. 10 shows the process of sharing computation operations between two iMDs. IMD 1 (1000) shares analytical capabilities between its SoC (1010) and the SoC (1040) of iMD2 (1030). The memory (1020) of iMD 1 is shared with the memory (1050) of iMD 2.

Figure 11:
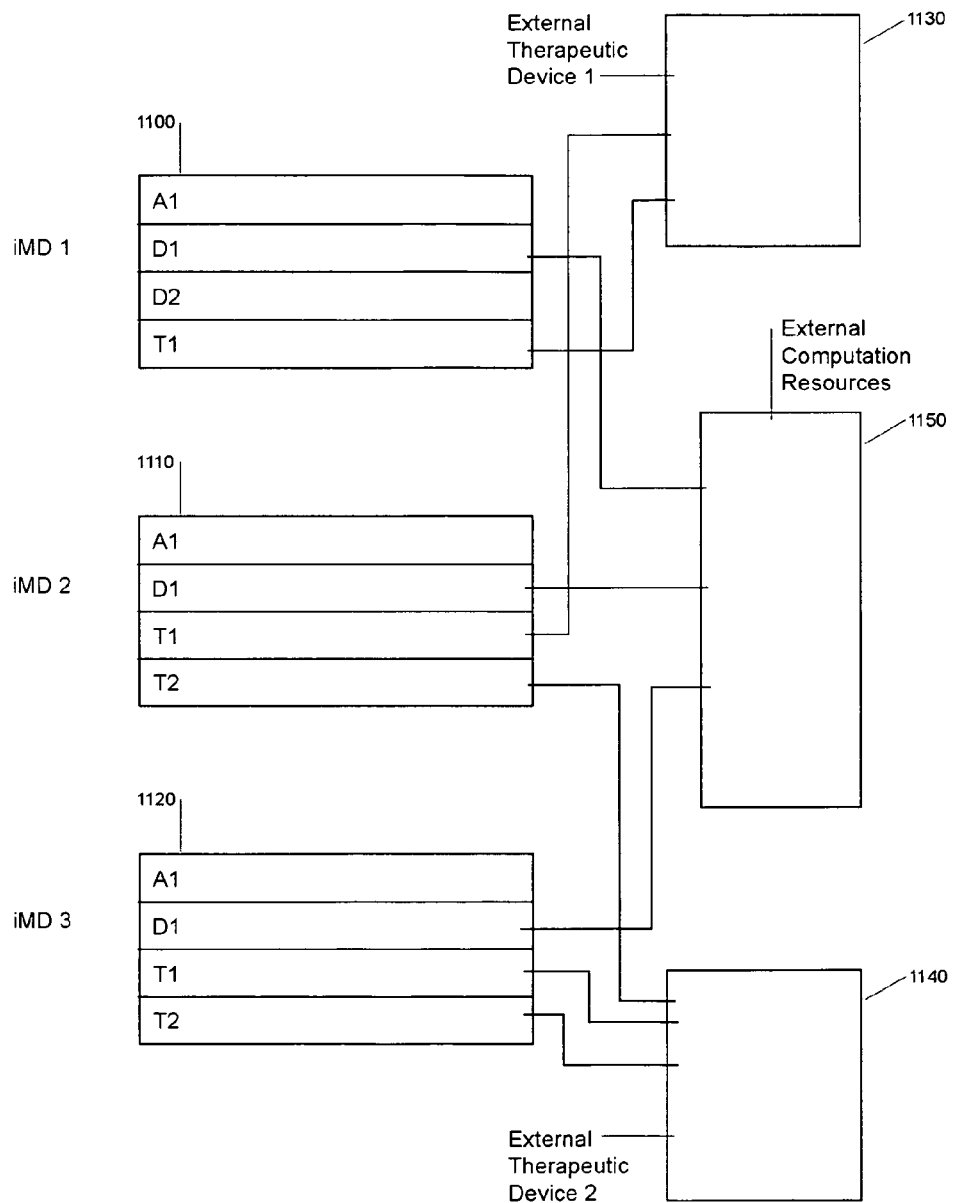
FIG. 11 is a schematic diagram showing the connection between three internal iMDs and external devices.

FIG. 11 shows the connection between three internal iMDs and external devices. IMD 1 (1100) is connected to external therapeutic device 1 (1130) at T1 and external computation resources (1150) at D1, iMD 2 (1110) is connected to external therapeutic device 1 at T1, external computation resources at D1 and external therapeutic device 1 (1140) at T2. IMD 3 (1120) is connected to external computation resources at D1 and external therapeutic device 2 at T1 and T2.

Figure 12:
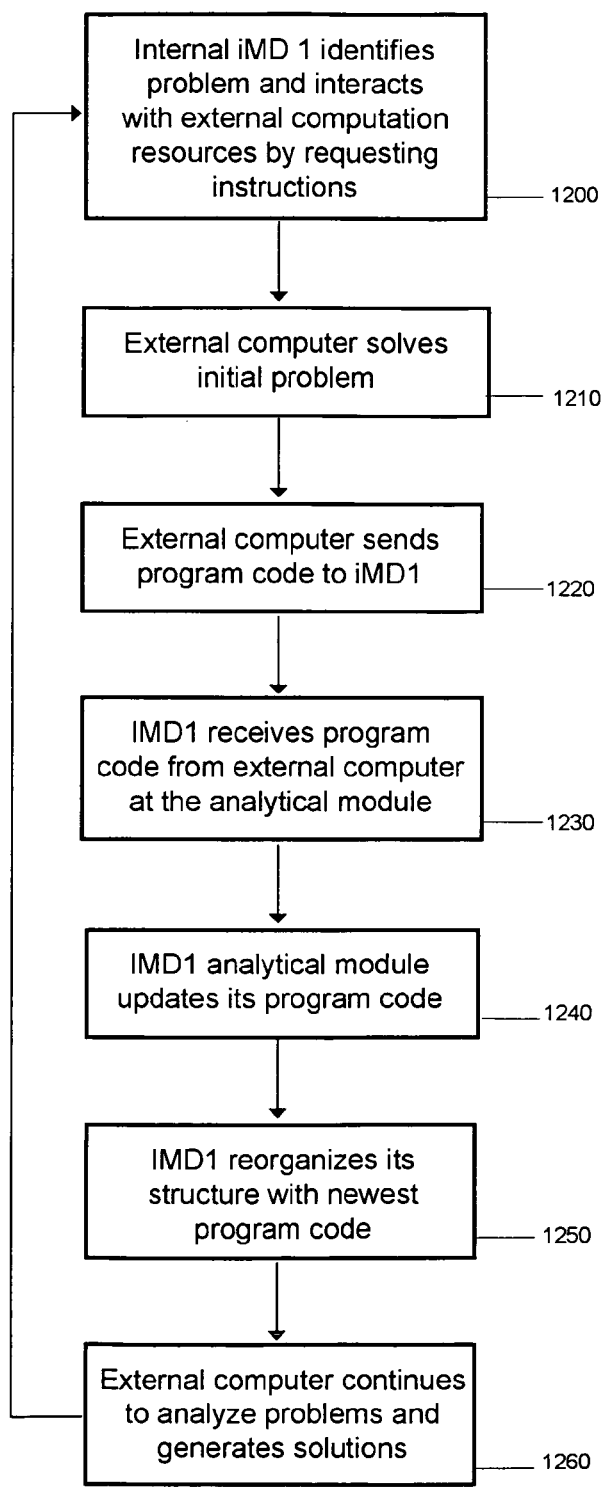
FIG. 12 is a flow chart describing the operational process of organizing an iMD to network with external computer resources.

FIG. 12 describes the operational process of organizing an iMD to network with external computer resources. After internal iMD 1 identifies a problem and interacts with external computation resources by requesting instructions (1200), the external computer solves an initial problem (1210) and sends program code to iMD 1 (1220). IMD 1 receives program code from the external computer at the analytical module (1230) and updates its program code (1240). IMD 1 reorganizes its structure with the newest code (1250) and the external computer continues to analyze problems as it generates solutions (1260).

Figure 13:
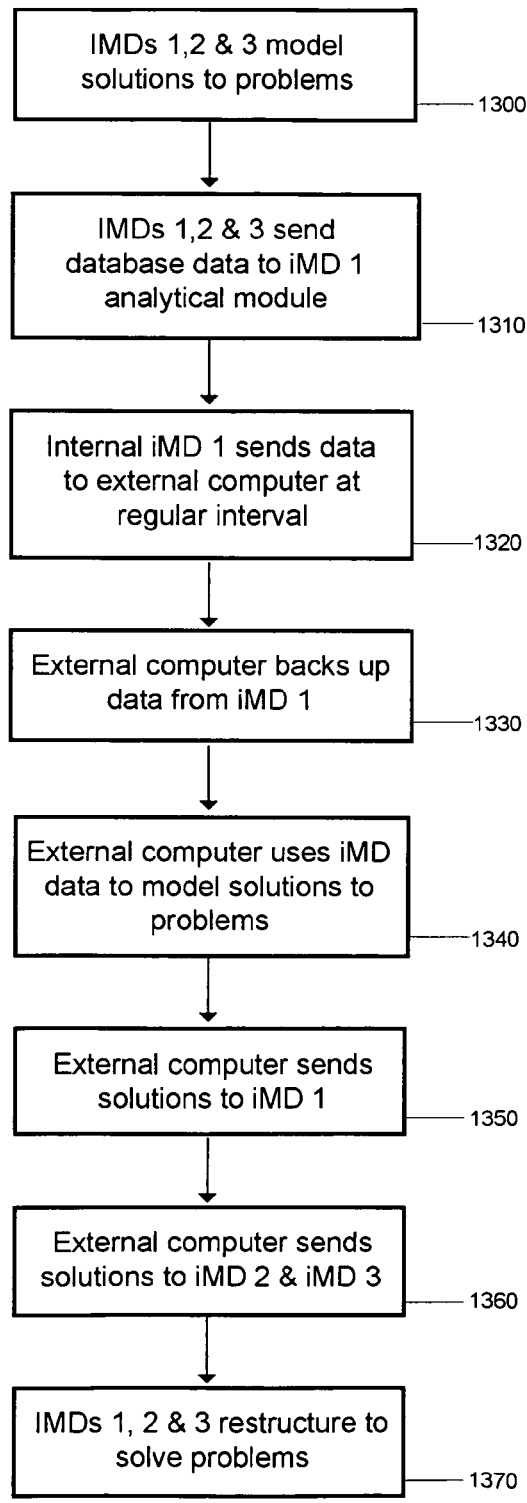
FIG. 13 is a flow chart showing the process of three iMDs solving problems by networking with external computer resources.

FIG. 13 describes the process of three iMDs solving problems by networking with external computer resources. Once iMDs 1, 2 and 3 model solutions to problems (1300), they send database data to iMD 1 analytical module (1310). The internal iMD 1 sends data to an external computer at regular intervals (1320) and the external computer backs up data from iMD 1 (1330). The external computer uses iMD data to model solutions to problems (1340) and then sends solutions to iMD 1 (1350). IMD 1 sends solutions to iMD 2 and iMD 3 (1360) and iMDs 1, 2 and 3 restructure to solve problems.

Figure 14:
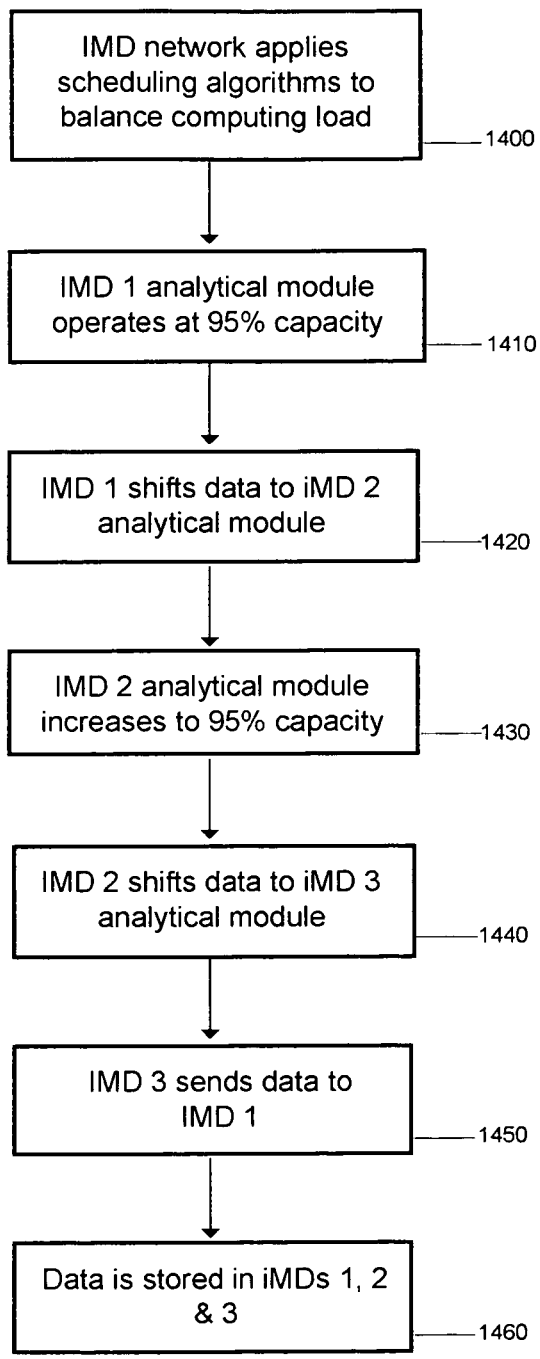
FIG. 14 is a flow chart showing the process of three iMDs sharing analytical resources.

FIG. 14 describes the process of three iMDs sharing analytical resources. The iMD network first applies scheduling algorithms to balance a computing load (1400). IMD1 analytical module then operates at 95% of capacity (1410) and iMD 1 shifts data to iMD 2 analytical module (1420). IMD 2 analytical module increases its capacity to 95% (1430) and iMD 2 shifts data to iMD 3 analytical module (1440). iMD sends data to iMD 1 (1450). Data is stored in iMDs 1, 2 and 3 (1460). When the iMD internal network is running at high capacity, it shifts its excess load capacity to external computational resources.

Figure 15:
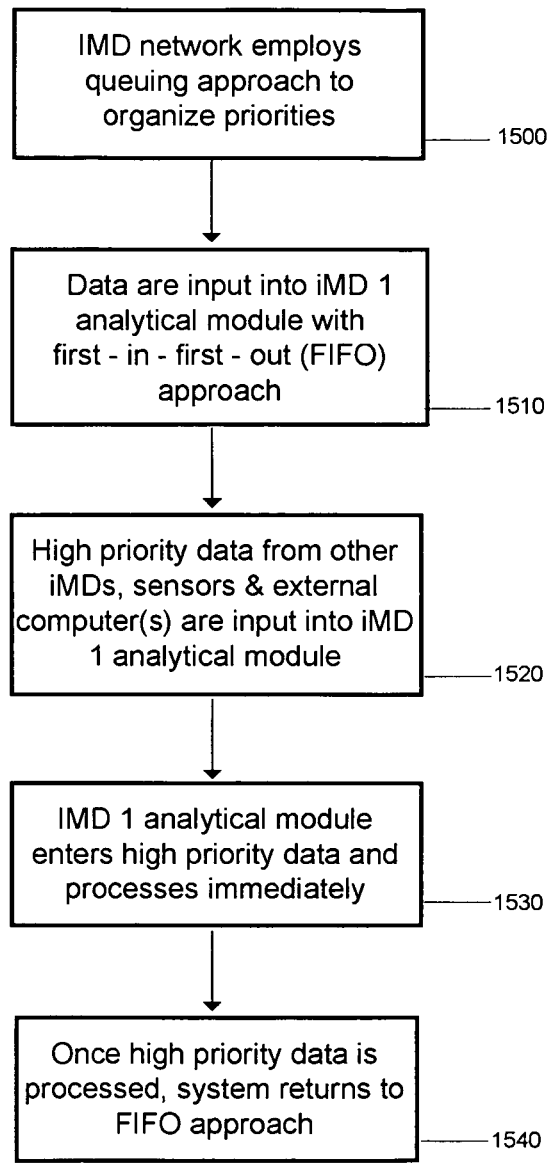
FIG. 15 is a flow chart showing the process of an iMD network organizing priorities to perform functions.

FIG. 15 describes the process of an iMD network organizing priorities to perform functions. The iMD network first employs a queuing approach to organize priorities (1500). Data are then input into iMD 1 analytical module with first-in-first-out (FIFO) approach (1510) and high priority data from other iMDs, sensors and external computer(s) are input into the iMD 1 analytical module (1520). The iMD 1 analytical module enters high priority data and processes the data immediately (1530). Once high priority data is processed, the system returns to the FIFO approach (1540).

Figure 16:
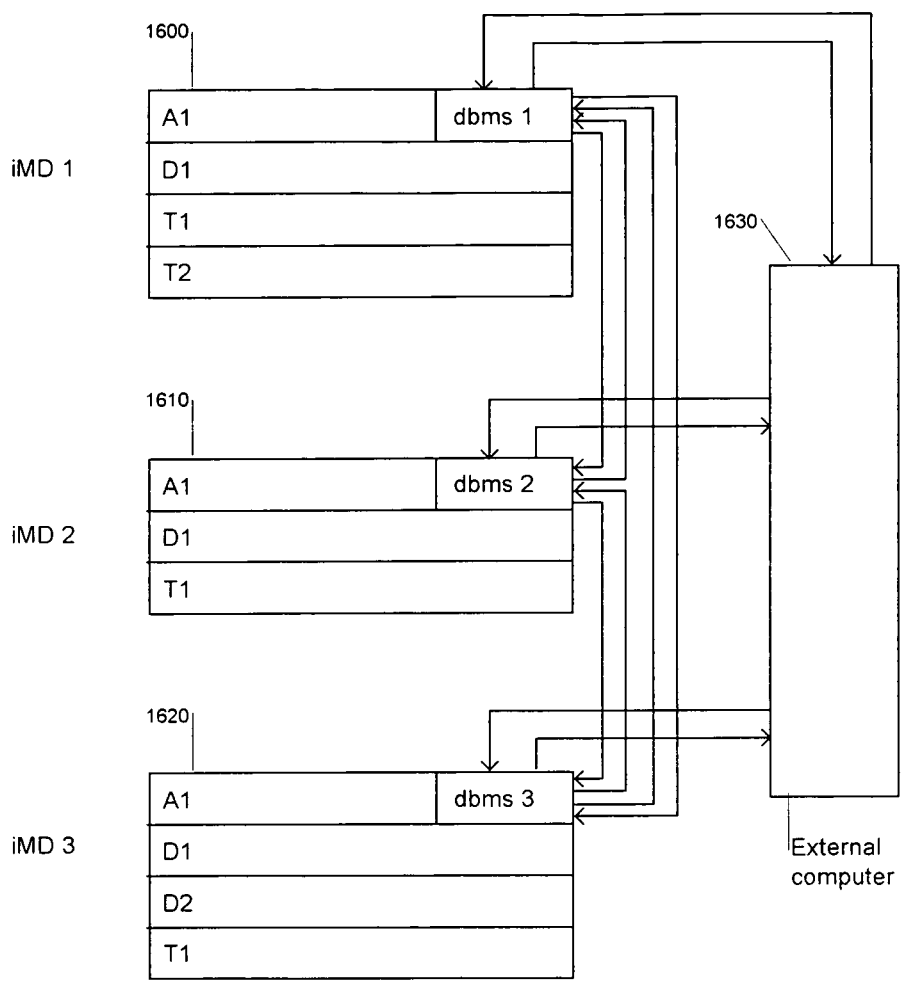
FIG. 16 is a schematic diagram showing the organizational process of sharing data among databases in a distributed iMD network.

FIG. 16 shows the organization process of sharing data among databases in a distributed iMD network. The databases in iMD 1 (1600) A1, iMD 2 (1610) A1 and iMD 3 (1620) A1 share data between each other and between the database management system in the external computer (1620).

Figure 17:
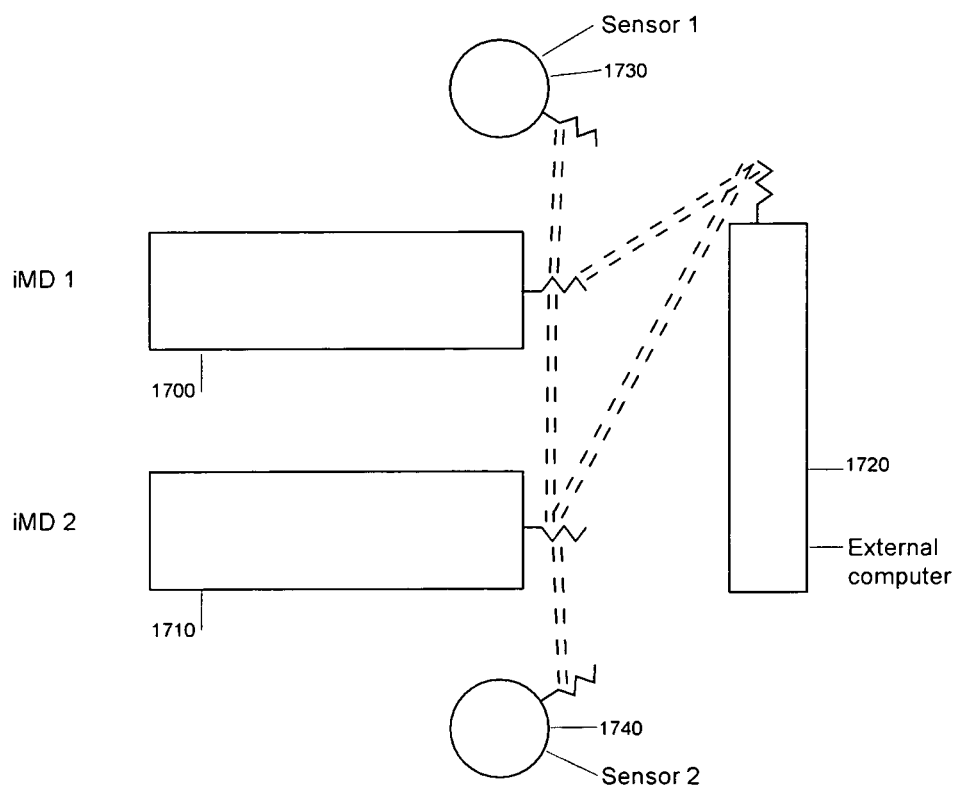
FIG. 17 is a schematic diagram showing the operation of wireless transmitters and receivers in an iMD network.

FIG. 17 shows the operation of a wireless transmitter and receivers in an iMD network. The transmitters and receivers in iMD 1 (1700) and iMD 2 (1710) send and receive signals between sensor 1 (1730), sensor 2 (1740) and the external computer (1720). The wireless iMD functions are particularly useful for interfacing between an iMD and an external computer as well as between iMDs and iMDs and iMDs and internal satellite devices. The wireless system is useful for updating program code at specific intervals and for exporting data for external computer resource analysis. In the wireless system, there is a need to integrate a strong security component to prevent unauthorized wireless access.

Figure 18:
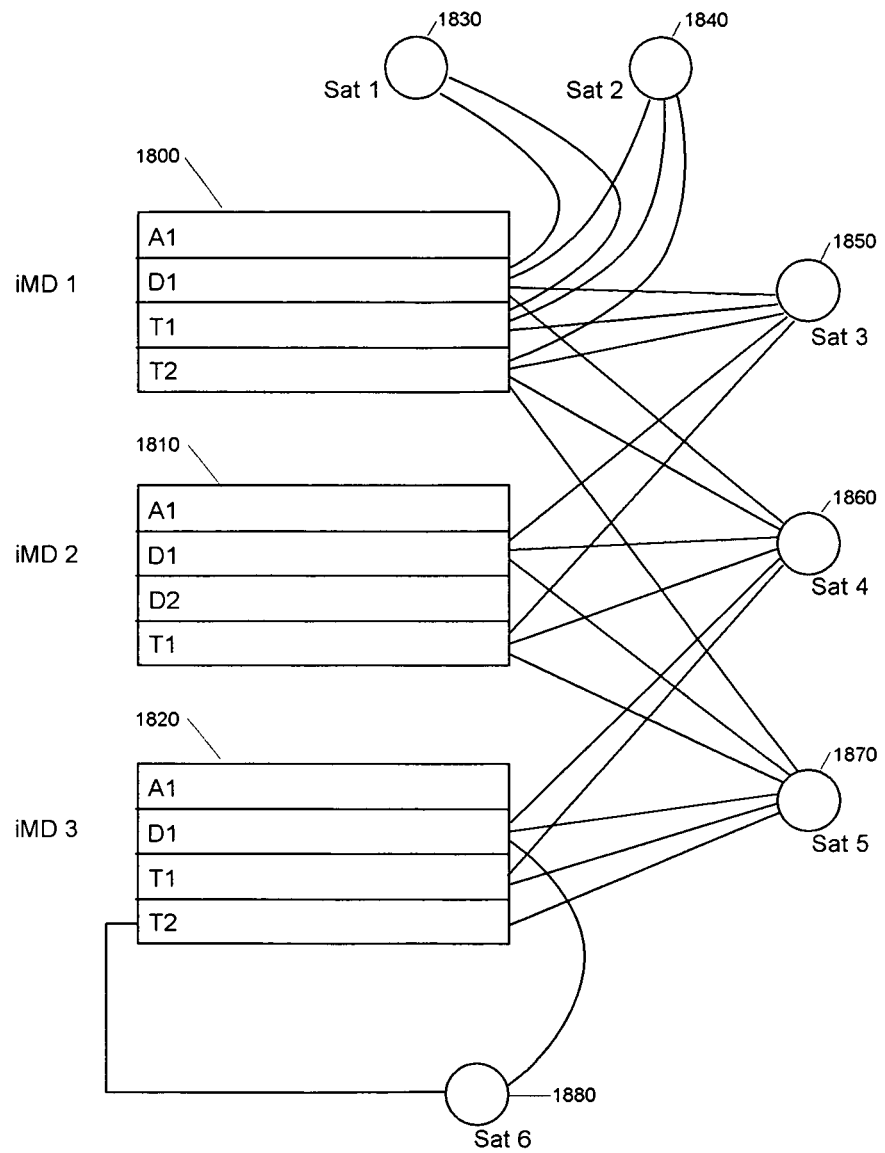
FIG. 18 is a schematic diagram showing micro-wires connected to devices in an internal iMD network.

FIG. 18 shows micro-wires connected to devices in an internal iMD network. The wires of iMD 1 (1800) D1 are connected to Sat 1, Sat 2, Sat 3 and Sat 3 (1820-1860), while the wires of iMD 1 T1 are connected to Sat 1, Sat 2 and Sat 3 and the wires of iMD 1 T2 are connected to Sat 2, Sat 3 and Sat 4. The wires of iMD 2 (1810) D1 and T2 are connected to Sat 3, Sat 4 and Sat 5 (1870). The wires of iMD 3 (1820) D1 are connected to Sat 4, Sat 5 and Sat 6 (1880), the wires of iMD 3 T1 are connected to Sat 4 and Sat 5 and the wires of iMD 3 T2 are connected to Sat 5 and Sat 6.

Figure 19:
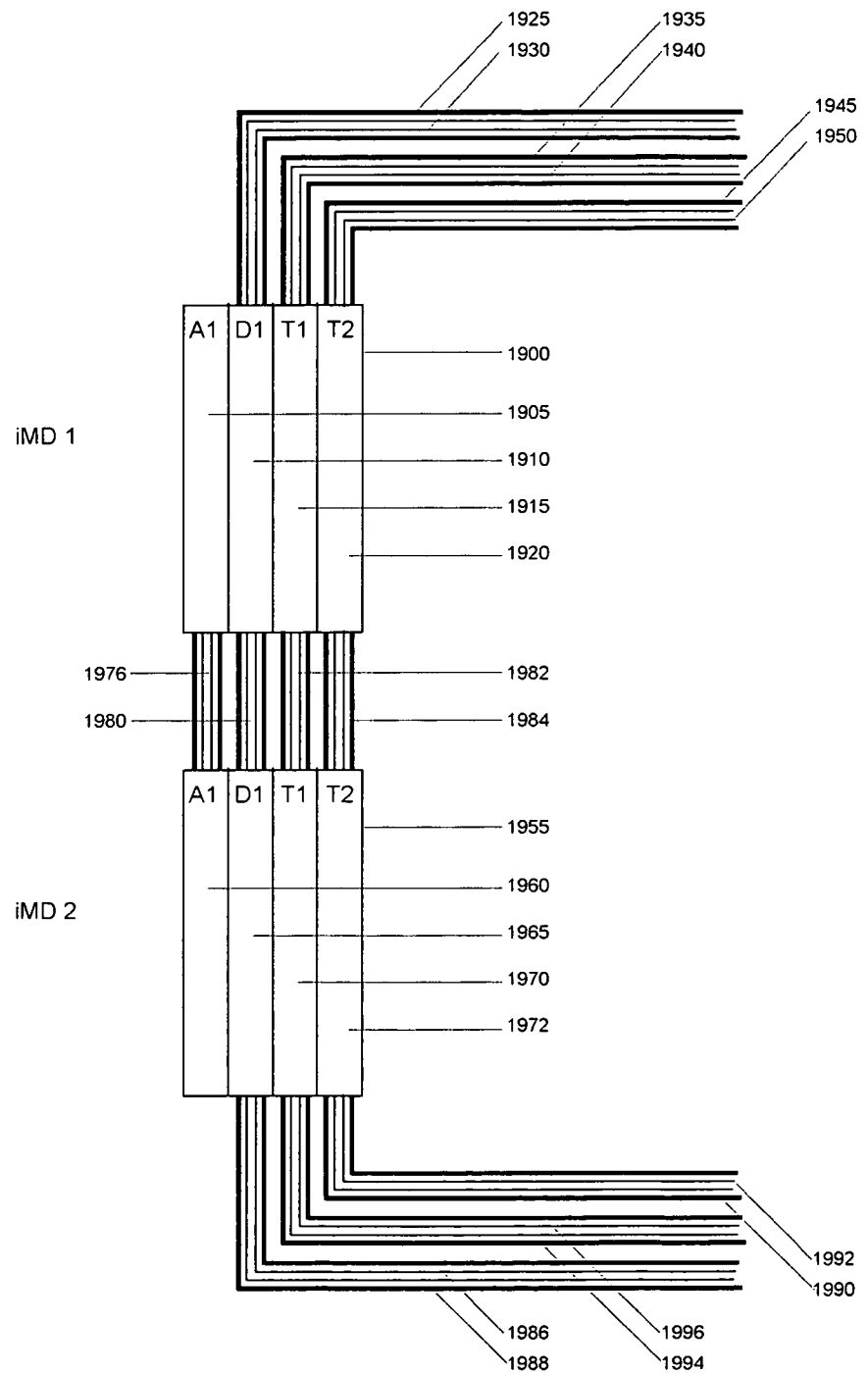
FIG. 19 is a schematic drawing describing the enclosure of interconnects in tubes in an iMD network.

FIG. 19 describes the enclosure of interconnects in tubes in an iMD network. In this case, the interconnects are connected between iMD 1 (1900) modules A1, D1, T1 and T2 and iMD 2 (1955) modules A1, D1, T1 and T2. Further, the modules at iMD 1 D1, T1 and T2 and the modules at iMD 2 D1, T1 and T2 are connected to external sources. Each enclosure contains at least two interconnects. In some cases, the enclosure contains tubing as well as electrical interconnects. The tubing is able to move fluids in one direction or in two directions. In some cases the unidirectional tubing is accompanied by complementary tubing for the sending and receiving of chemicals or biologicals.

Figure 20:
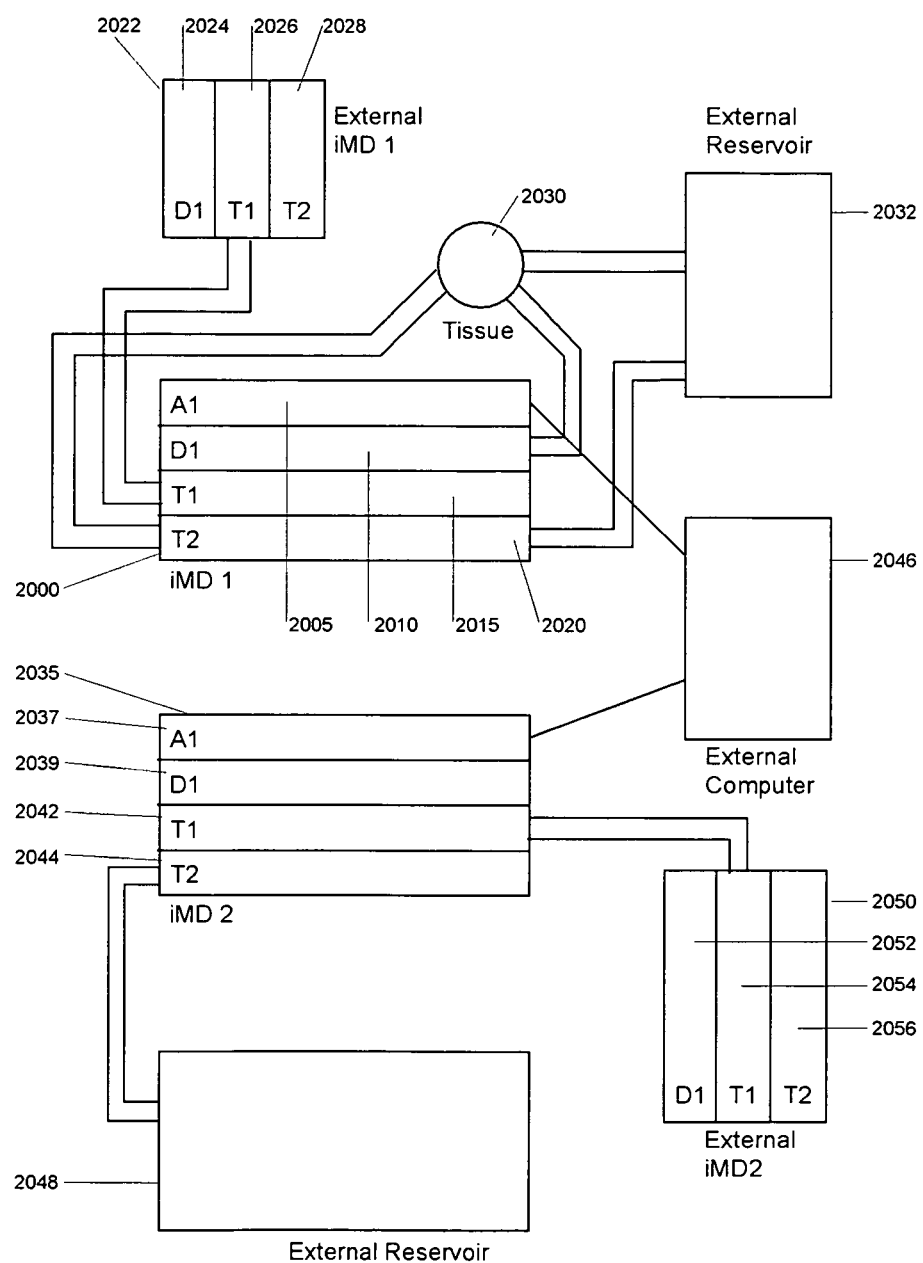
FIG. 20 is a schematic diagram showing the interconnections between internal and external iMDs.

FIG. 20 shows the interconnections between internal and external iMDs. Internal iMD 1 (2000) T1 (2015) is connected to external iMD 1 (2022) T1 (2026). Internal iMD 1 T2 is connected to tissue (2030) and to external reservoir (2032). Internal iMD 1 D1 is connected to tissue. Internal iMD 1 A1 is connected to the external computer (2046). The external reservoir is connected to tissue. Internal iMD 2 A1 (2035) is connected to the external computer. Internal iMD 2 T1 (2042) is connected to external iMD 2 (2050) T1 (2054). IMD 2 T2 (2044) is connected to an external reservoir (2048).

Figure 21:
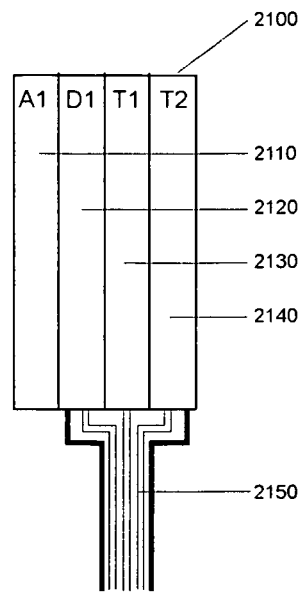
FIG. 21 is a drawing showing the apparatus of external shared tubing in an iMD.

FIG. 21 shows the apparatus of external shared tubing in an iMD. The sharing tubing mechanism (2150) is shielded and is shared between D1 (2120), T1 (2130) and T2 (2140).

Figure 22:
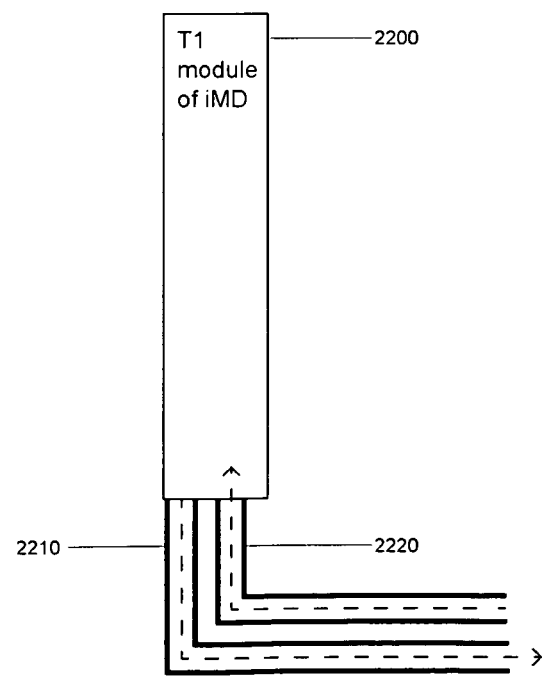
FIG. 22 is a schematic diagram showing a cut out of microtubing for therapeutic module for sending and extracting chemicals and biologicals.

FIG. 22 shows a cut out of micro-tubing for a therapeutic module for sending and extracting chemicals and biologicals. The T1 module (2200) has tubing (2210) that exports fluids and tubing (2220) that imports fluids.

Figure 23:
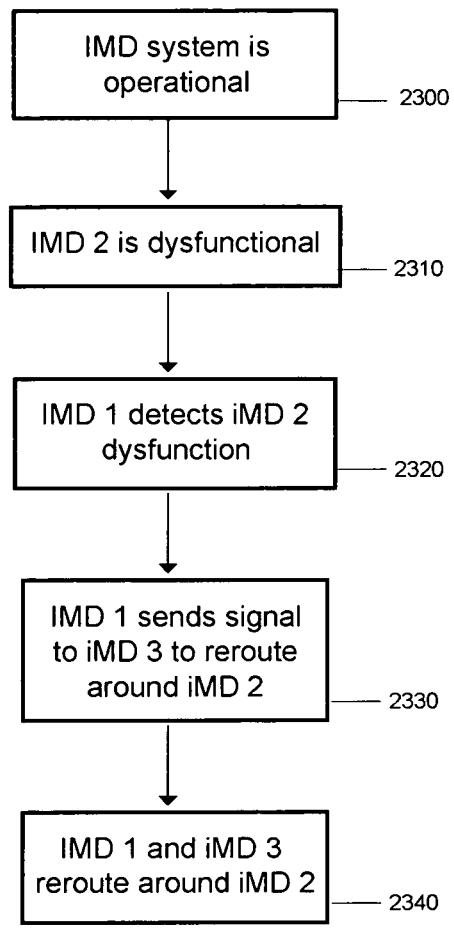
FIG. 23 is a flow chart describing the process of rerouting iMD operations around a dysfunctional iMD apparatus.

FIG. 23 describes the process of rerouting iMD operations around a dysfunctional iMD apparatus. Though the iMD system is initially operational (2300), iMD 2 becomes dysfunctional (2310) and iMD 1 detects iMD 2 dysfunction (2320). IMD 1 sends a signal to iMD 3 to reroute around iMD 2 (2330) and iMD 1 and iMD 3 reroute around iMD 2 (2340). Because the modules are independent, the iMD network may reroute around specific modules as well as whole iMDs.

In another embodiment of the system, when a new medical device satellite or a new iMD is added to the system, the network recalibrates the system to add the new components. This involves registering the functional capabilities with each SoC and database in the system.

Figure 24:
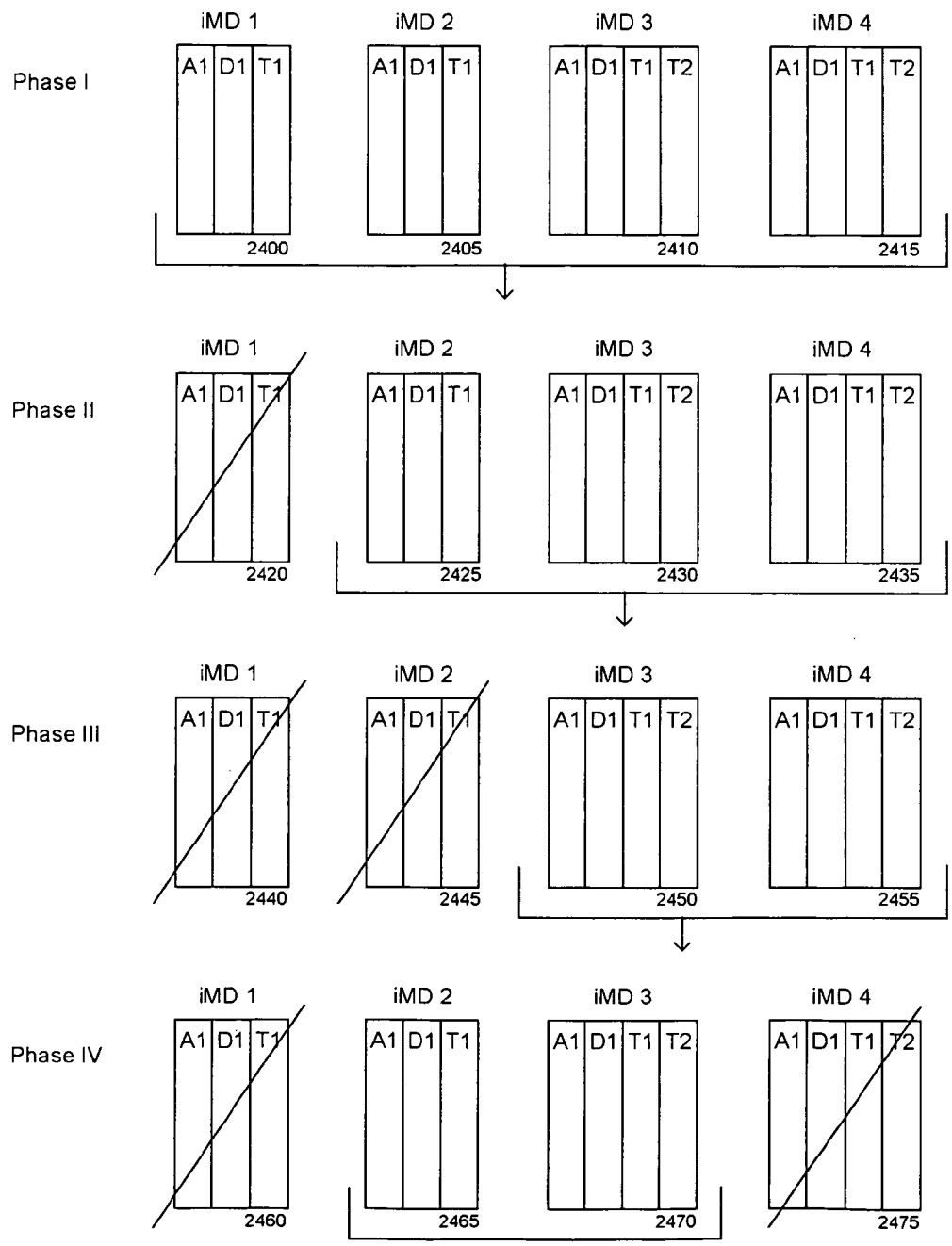
FIG. 24 is a schematic diagram showing four phases of a process of reorganization to accommodate the loss, and reconstitution, of iMDs in a network.

FIG. 24 shows four phases of a process of reorganization to accommodate the loss, and reconstitution, of iMDs in a network. In phase I all four iMDs (2400, 2405, 2410 and 2415) are operational. In phase II, iMD 1 (2420) is dysfunctional and removed from the network. In phase III, iMD 1 and iMD 2 (2445) are both removed from the network. In phase IV, while iMD 1 is still dysfunctional, iMD 2 has been restored, while iMD 4 is also removed from the network. The remaining iMDs in the network are iMD 2 and iMD 3. Though this figure shows the reorganization of an iMD network around iMDs, in one embodiment, the network reorganizes around dysfunctional iMD modules.

Figure 25:
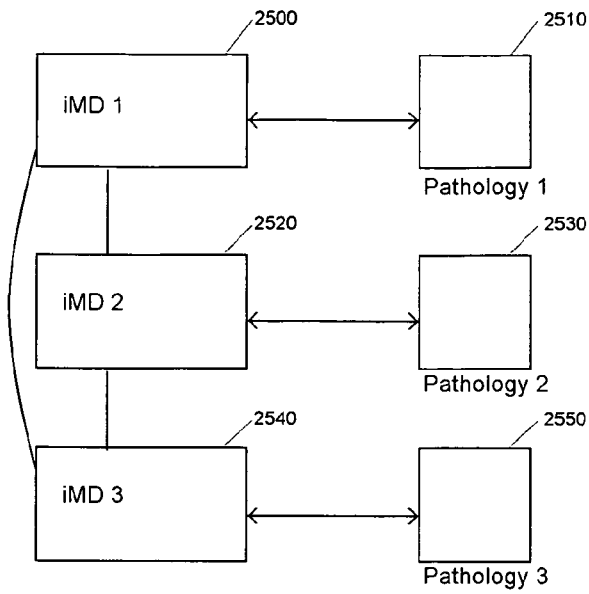
FIG. 25 is a schematic diagram showing the parallel simultaneous pathology interactions of an iMD network.

FIG. 25 shows the parallel simultaneous pathology interactions of an iMD network. In this drawing, the three iMDs (2500, 2520 and 2540) are interconnected while each iMD deals with a pathology (2510, 2530 and 2550).

Figure 26:
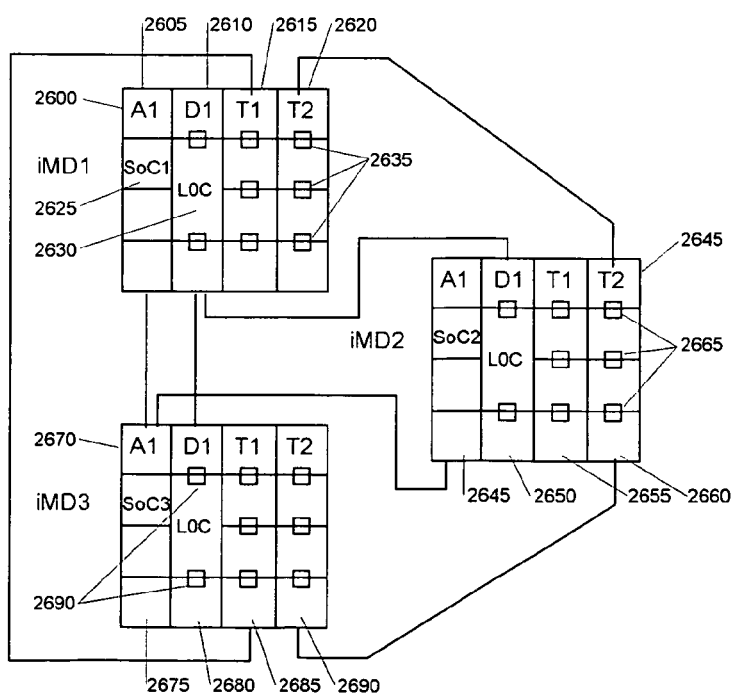
FIG. 26 is a schematic diagram showing the stoplight functions at valve connections between iMDs in a network configuration.

FIG. 26 shows the stoplight functions at valve connections between iMDs in a network configuration. The sensors (2635, 2665 and 2690) are configured in a grid in each iMD at the junction of specific active compartments. The sensors are operated by the SoC of each iMD. While the therapeutic modules of each iMD are interconnected, the diagnostic modules of each iMD are interconnected and the analytical modules of each iMD are interconnected, the sensors operate to control the flow of data and fluids between the iMDs. Much like a stop light system for traffic, the integrated sensor grid in the iMD network operates by turning on and off in a controlled pattern to facilitate the flow of data and fluids between the components of the system by modulating the operation of valves and electrical connections between the compartments. This model develops a grid switching control system for regulating flow control and electrical control in the iMD.

Figure 27:
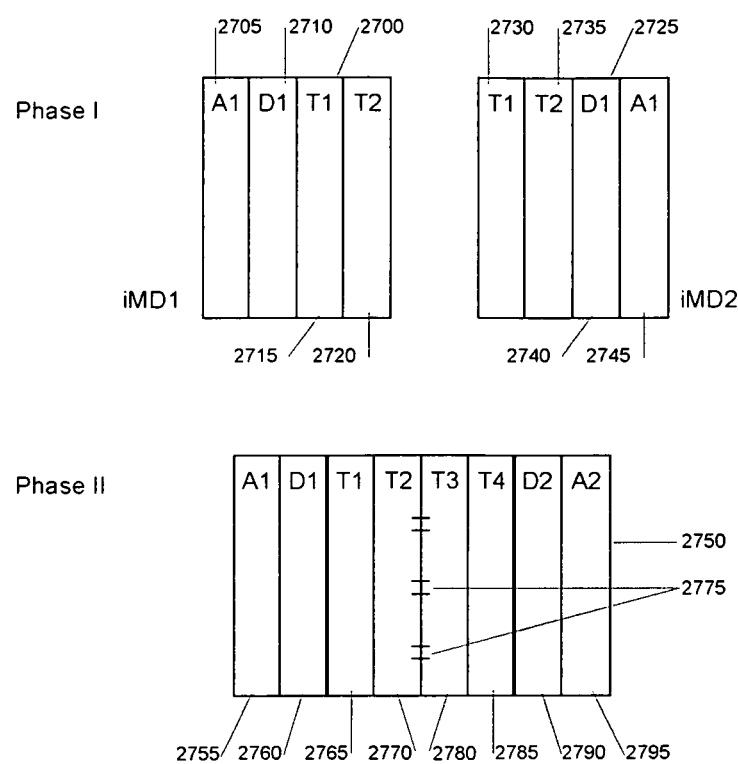
FIG. 27 is a schematic diagram showing the process of combining and reconfiguring of therapeutic modules of two iMDs.

FIG. 27 shows the process of combining and reconfiguring the therapeutic modules of two iMDs. In phase I, two independent iMDs (2700 and 2725) are shown. In phase II, the iMD 2 T1 is combined with the iMD 1 T2 to become the iMD X (2750) T3, while the iMD 2 T2 becomes the iMD X T4. The iMD 1 T2 and iMD 2 T1 are attached at seams that share fluids and electrical connections at 2775 and 2780.

I claim:

1. A system for organizing modular medical devices in a network, comprising:
a plurality of medical devices configured in a network, including a central medical device and at least one satellite medical device;
wherein the central medical device comprises modules including at least one diagnostic module, at least one analytical module, and at least one therapeutic module,
wherein the at least one satellite medical device also includes at least one diagnostic, analytical or therapeutic module,
a set of electrical interconnects configured to connect the central medical device, the modules and the at least one satellite medical devices;

a set of fluid interconnects configured to facilitate the transfer of biological or chemical fluids between the central medical device, the modules and the at least one satellite medical devices;
wherein the central medical device controls the at least one satellite medical devices in the network utilizing a system on a chip (SoC),
wherein the at least one diagnostic module includes a lab-on-a-chip (LOC) apparatus,
wherein the at least one diagnostic module receives cell, gene, protein or RNA samples utilizing the LOC apparatus, extracts data from the samples and forwards the extracted sample data to the at least one analytical module,
wherein the at least one analytical module is configured to identify a pathology and build a remedial model based on the extracted sample data, and
wherein the at least one satellite medical device forwards the extracted sample data, the identified pathology and the remedial model to the central medical device.

2. The system of claim 1,
wherein the functions of the at least one analytical module are carried out jointly between the central medical device and the at least one satellite medical device.

3. The system of claim 1,
wherein the received samples are forwarded to the at least one diagnostic module of the central medical device or to the at least one diagnostic module of the at least one satellite medical device.

4. The system of claim 1,
wherein the functions of the at least one analytical module are performed by the central medical device.

5. The system of claim 1,
wherein at least two pathologies are identified by at least two analytical modules of the central medical device and the at least one satellite medical device simultaneously.

6. The system of claim 1,
wherein the at least one therapeutic module obtains refills of chemicals and biologicals from the at least one satellite medical device via the set of fluid interconnects.

7. A system for organizing modular medical devices in a network, comprising:
a plurality of medical devices configured in a network, including a central medical device and at least one satellite medical device;
at least one external computer,
wherein the central medical device comprises modules including at least one diagnostic module and at least one therapeutic module,
wherein the at least one satellite medical device also includes at least one diagnostic or therapeutic module,
wherein the at least one external computer includes at least one analytical module;
a set of electrical interconnects configured to connect the central medical device, the modules and the at least one satellite medical device;
a set of radio frequency transceivers configured to wirelessly transmit and receive data between the central medical device, the modules, the at least one satellite medical device and the at least one external computer;
a set of fluid interconnects configured to facilitate the transfer of biological or chemical fluids between the central medical device, the modules and the at least one satellite medical device,
wherein the at least one central medical device is configured to control the at least one satellite medical device in the network utilizing a system on a chip (SoC),
wherein the at least one diagnostic module includes a lab-on-a-chip (LOC) apparatus,
wherein the at least one diagnostic module receives cell, gene, protein or RNA samples utilizing the LOC apparatus, extracts data from the samples and forwards the extracted sample data to the at least one analytical module stored in the external computer,
wherein the at least one analytical module identifies a pathology and builds a remedial model based on the extracted data and forwards the remedial model to the at least one therapeutic module, and
wherein the at least one therapeutic module combines chemicals and biologicals based on the remedial model and administers the combination to a patient.

8. The system of claim 7,
wherein the at least one diagnostic module transmits received samples to at least one other diagnostic module via the set of fluid interconnects.

9. The system of claim 7,
wherein the extracted sample data are transmitted from at least two diagnostic modules to the at least one external computer.

10. The system of claim 7,
wherein the at least one therapeutic module transmits chemical or biological fluids to at least one other therapeutic module via the set of fluid interconnects.

11. The system of claim 7,
wherein at least two diagnostic modules receive samples simultaneously.

12. The system of claim 7,
wherein at least one therapeutic module obtains refills of chemicals and biologicals from the at least one satellite medical device via the set of fluid interconnects.

13. A system for organizing modular medical devices in a network, comprising:
a plurality of medical devices configured in a network, including a central medical device and at least one satellite medical device,
wherein the central medical device comprises modules including at least one diagnostic module, at least one analytical module and at least one therapeutic module,
wherein the at least one satellite medical device also includes at least one diagnostic, analytical or therapeutic module,
wherein the central medical device, the modules and the at least one satellite medical device are connected via a set of electrical interconnects or a set of radio frequency transceivers;
a set of fluid interconnects configured to facilitate the transfer of biological or chemical fluids between the central medical device, the modules and the at least one satellite medical device,
wherein the at least one central medical device is configured to control the at least one satellite medical devices in the network utilizing a system on a chip (SoC),
wherein the at least one diagnostic module includes a lab-on-a-chip (LOC) apparatus,
wherein the at least one diagnostic module receives cell, gene, protein or RNA samples utilizing the LOC apparatus, extracts data from the samples and forwards the extracted sample data to the at least one analytical module,
wherein the at least one analytical module identifies a pathology and builds a remedial model based on the extracted sample data and forwards the remedial model to the at least one therapeutic module, and wherein the at least one therapeutic module in the medical device network combines chemicals and biologicals based on the remedial model and administers the combination to a patient.

14. The system of claim 13,
wherein at least two LOC apparatuses receive samples and extract sample data.

15. The system of claim 13,
wherein the extracted sample data are transmitted between at least two diagnostic modules wirelessly via the set of radio frequency transceivers.

16. The system of claim 13,
wherein the at least one therapeutic module transmits chemical or biological fluids to at least one other therapeutic module via the set of fluid interconnects.

17. The system of claim 13,
wherein at least two diagnostic modules in the medical device network receive samples simultaneously.

18. The system of claim 13,
wherein at least one therapeutic module obtains refills of chemicals and biologicals from the at least one satellite medical device via the set of fluid interconnects.

19. The system of claim 13,
wherein the at least one diagnostic module transmits received samples to at least one other diagnostic module via the set of fluid interconnects.

* * * * *